(12) United States Patent
Piskun

(10) Patent No.: US 11,071,534 B2
(45) Date of Patent: Jul. 27, 2021

(54) SYSTEM FOR A MINIMALLY-INVASIVE TREATMENT WITHIN A BODY LUMEN

(71) Applicant: BOSTON SCIENTIFIC SCIMED, INC., Maple Grove, MN (US)

(72) Inventor: Gregory Piskun, Morganville, NJ (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 405 days.

(21) Appl. No.: 15/858,434

(22) Filed: Dec. 29, 2017

(65) Prior Publication Data

US 2018/0185018 A1 Jul. 5, 2018

Related U.S. Application Data

(60) Provisional application No. 62/440,502, filed on Dec. 30, 2016.

(51) Int. Cl.
*A61B 17/02* (2006.01)
*A61B 1/00* (2006.01)
(Continued)

(52) U.S. Cl.
CPC ...... *A61B 17/0218* (2013.01); *A61B 1/00082* (2013.01); *A61B 1/00087* (2013.01);
(Continued)

(58) Field of Classification Search
CPC ...... A61B 1/00089; A61B 2017/00296; A61B 1/3132; A61B 1/31; A61B 17/0218;
(Continued)

(56) References Cited

U.S. PATENT DOCUMENTS

| 1,621,159 A | 3/1927 | Evans |
| 3,517,128 A | 6/1970 | Hines |

(Continued)

FOREIGN PATENT DOCUMENTS

| CN | 201200436 Y | 3/2009 |
| CN | 102018493 A | 4/2011 |

(Continued)

OTHER PUBLICATIONS

International Search Report and Written Opinion for International Application No. PCT/US2016/016911, dated May 6, 2016, 9 pages.
(Continued)

*Primary Examiner* — John P Leubecker
*Assistant Examiner* — Shankar Raj Ghimire
(74) *Attorney, Agent, or Firm* — Kacvinsky Daisak Bluni PLLC

(57) ABSTRACT

A system for endoscopic surgery within a body lumen of a patient including a flexible catheter having an expandable region at a distal portion and an access opening. The expandable region is expandable from a collapsed insertion configuration to an expanded configuration to provide an expanded chamber on a first side of the catheter. The access opening is positioned on a second side opposite the first side to provide a window to access target tissue. The catheter includes a lumen dimensioned to receive an endoscopic instrument therethrough such that a distal end of the endoscopic instrument is positionable within the expanded chamber and angled laterally within the expanded chamber to access the target tissue through the window.

19 Claims, 17 Drawing Sheets

(51) Int. Cl.
*A61B 1/018* (2006.01)
*A61M 25/10* (2013.01)
*A61B 1/313* (2006.01)
*A61B 17/00* (2006.01)
*A61B 17/22* (2006.01)
*A61B 90/00* (2016.01)
*A61B 90/92* (2016.01)
*A61B 17/29* (2006.01)

(52) U.S. Cl.
CPC ...... *A61B 1/00135* (2013.01); *A61B 1/00154* (2013.01); *A61B 1/018* (2013.01); *A61B 1/3132* (2013.01); *A61B 90/92* (2016.02); *A61B 2017/0034* (2013.01); *A61B 2017/00269* (2013.01); *A61B 2017/00292* (2013.01); *A61B 2017/00327* (2013.01); *A61B 2017/00331* (2013.01); *A61B 2017/00818* (2013.01); *A61B 2017/0225* (2013.01); *A61B 2017/22071* (2013.01); *A61B 2017/2906* (2013.01); *A61B 2090/0811* (2016.02); *A61M 25/1002* (2013.01)

(58) Field of Classification Search
CPC ............ A61B 1/00082; A61B 1/00087; A61B 1/00135; A61B 1/00154; A61B 1/018; A61B 2090/0811; A61B 2017/00269; A61B 2017/00292; A61B 2017/00327; A61B 2017/00331; A61B 2017/0034; A61B 2017/00818; A61B 2017/0225; A61B 2017/2071; A61B 2017/2906; A61B 25/1002; A61M 25/1002
See application file for complete search history.

(56) References Cited

U.S. PATENT DOCUMENTS

| | | |
|---|---|---|
| 4,040,413 A | 8/1977 | Ohshiro |
| 4,083,369 A | 4/1978 | Sinnreich |
| 4,224,929 A | 9/1980 | Furihata |
| 4,295,464 A | 10/1981 | Shihata |
| 4,519,403 A | 5/1985 | Dickhudt |
| 4,611,594 A | 9/1986 | Grayhack et al. |
| 4,966,596 A | 10/1990 | Kuntz et al. |
| 5,025,778 A | 6/1991 | Silverstein et al. |
| 5,059,199 A | 10/1991 | Okada et al. |
| 5,087,265 A | 2/1992 | Summers |
| 5,112,310 A | 5/1992 | Grobe |
| 5,197,971 A | 3/1993 | Bonutti |
| 5,386,817 A | 2/1995 | Jones |
| 5,411,508 A | 5/1995 | Bessler et al. |
| 5,423,830 A | 6/1995 | Schneebaum et al. |
| 5,558,642 A * | 9/1996 | Schweich, Jr. ... A61M 16/0431 604/103.01 |
| 5,655,698 A | 8/1997 | Yoon |
| 5,716,321 A | 2/1998 | Kerin et al. |
| 5,722,103 A | 3/1998 | Walega |
| 5,766,151 A * | 6/1998 | Valley ............ A61M 25/0155 604/103.07 |
| 5,776,097 A * | 7/1998 | Massoud ......... A61B 17/12022 604/500 |
| 5,947,983 A * | 9/1999 | Solar ............. A61B 17/0469 604/22 |
| 5,954,731 A | 9/1999 | Yoon |
| 5,997,547 A | 12/1999 | Nakao et al. |
| 6,009,877 A | 1/2000 | Edwards |
| 6,042,596 A | 3/2000 | Bonutti |
| 6,119,913 A | 9/2000 | Adams et al. |
| 6,142,931 A | 11/2000 | Kaji |
| 6,142,933 A | 11/2000 | Longo et al. |
| 6,203,552 B1 | 3/2001 | Bagley et al. |
| 6,214,024 B1 | 4/2001 | Houser |
| 6,264,086 B1 | 7/2001 | McGuckin, Jr. |
| 6,302,311 B1 | 10/2001 | Adams et al. |
| 6,343,731 B1 | 2/2002 | Adams et al. |
| 6,405,732 B1 | 6/2002 | Edwards et al. |
| 6,423,058 B1 | 7/2002 | Edwards et al. |
| 6,428,473 B1 | 8/2002 | Leonard et al. |
| 6,494,881 B1 | 12/2002 | Bales et al. |
| 6,616,603 B1 | 9/2003 | Fontana |
| 6,695,198 B2 | 2/2004 | Adams et al. |
| 6,805,273 B2 | 10/2004 | Bilotti et al. |
| 6,808,491 B2 | 10/2004 | Kortenbach et al. |
| 6,840,423 B2 | 1/2005 | Adams et al. |
| 6,866,178 B2 | 3/2005 | Adams et al. |
| 6,874,669 B2 | 4/2005 | Adams et al. |
| 6,913,610 B2 | 7/2005 | Nakao |
| 6,923,806 B2 | 8/2005 | Hooven et al. |
| 6,938,814 B2 | 9/2005 | Sharma et al. |
| 7,014,646 B2 | 3/2006 | Adams |
| 7,059,331 B2 | 6/2006 | Adams et al. |
| 7,169,115 B2 | 1/2007 | Nobis et al. |
| 7,276,066 B2 | 10/2007 | Ouchi |
| 7,396,329 B2 | 7/2008 | Nakao |
| 7,445,598 B2 | 11/2008 | Orban, III |
| 7,918,787 B2 | 4/2011 | Saadat |
| 7,959,559 B2 * | 6/2011 | Yamaya ............ A61B 1/00082 600/104 |
| 8,007,508 B2 | 8/2011 | Cox |
| 8,088,139 B2 | 1/2012 | Scopton et al. |
| 8,277,373 B2 | 10/2012 | Maahs et al. |
| 8,506,479 B2 | 8/2013 | Piskun et al. |
| 8,517,933 B2 | 8/2013 | Mohr |
| 8,608,652 B2 | 12/2013 | Voegele et al. |
| 8,764,630 B2 | 7/2014 | Yamatani |
| 8,764,785 B2 | 7/2014 | Scopton et al. |
| 8,777,961 B2 | 7/2014 | Cabrera et al. |
| 8,932,326 B2 | 1/2015 | Riina et al. |
| 8,979,884 B2 | 3/2015 | Milsom et al. |
| 9,050,004 B2 | 6/2015 | Diao et al. |
| 9,161,746 B2 | 10/2015 | Piskun et al. |
| 9,168,053 B2 | 10/2015 | Cox |
| 9,259,233 B2 | 2/2016 | Gruber et al. |
| 9,370,379 B2 | 6/2016 | Osman |
| 9,375,224 B2 * | 6/2016 | Jansen ............ A61B 17/00234 |
| 9,565,998 B2 * | 2/2017 | Piskun ............... A61B 1/00082 |
| 9,661,984 B2 | 5/2017 | Piskun |
| 10,286,190 B2 * | 5/2019 | Moelgaard-Nielsen ..................... A61M 25/10 |
| 2001/0004947 A1 | 6/2001 | Lemke et al. |
| 2001/0047169 A1 | 11/2001 | McGuckin, Jr. et al. |
| 2001/0049497 A1 | 12/2001 | Kalloo et al. |
| 2002/0123748 A1 | 9/2002 | Edwards et al. |
| 2002/0183593 A1 | 12/2002 | Chin et al. |
| 2002/0193660 A1 | 12/2002 | Weber et al. |
| 2003/0023143 A1 | 1/2003 | Abe et al. |
| 2003/0050663 A1 | 3/2003 | Khachin et al. |
| 2003/0074015 A1 | 4/2003 | Nakao |
| 2003/0135230 A1 | 7/2003 | Massey et al. |
| 2003/0225432 A1 | 12/2003 | Baptiste et al. |
| 2003/0225433 A1 | 12/2003 | Nakao |
| 2004/0034278 A1 | 2/2004 | Adams |
| 2004/0082859 A1 | 4/2004 | Schaer |
| 2004/0158263 A1 * | 8/2004 | McAlister ............ A61B 17/068 606/139 |
| 2004/0204725 A1 | 10/2004 | Bayer |
| 2004/0249367 A1 | 12/2004 | Saadat et al. |
| 2005/0177105 A1 * | 8/2005 | Shalev ............ A61M 25/1002 604/104 |
| 2005/0182438 A1 * | 8/2005 | Scopton ............ A61B 1/0008 606/194 |
| 2005/0234297 A1 | 10/2005 | Devierre et al. |
| 2005/0234299 A1 | 10/2005 | Eitenmuller et al. |
| 2005/0240147 A1 | 10/2005 | Makower et al. |
| 2005/0251111 A1 * | 11/2005 | Saito .................... A61B 17/29 606/1 |
| 2005/0251177 A1 | 11/2005 | Saadat et al. |
| 2005/0272977 A1 | 12/2005 | Saadat et al. |
| 2006/0074277 A1 | 4/2006 | Yoshida |
| 2006/0100480 A1 | 5/2006 | Ewers et al. |
| 2006/0184191 A1 * | 8/2006 | O'Brien ............ A61M 25/1002 606/192 |

(56) References Cited

U.S. PATENT DOCUMENTS

| | | |
|---|---|---|
| 2006/0189845 A1 | 8/2006 | Maahs et al. |
| 2006/0191975 A1 | 8/2006 | Adams et al. |
| 2006/0247662 A1 | 11/2006 | Schwartz et al. |
| 2006/0264706 A1 | 11/2006 | Piskun |
| 2007/0005093 A1 | 1/2007 | Cox |
| 2007/0021778 A1 | 1/2007 | Carly |
| 2007/0255207 A1 | 11/2007 | Hangai et al. |
| 2007/0287886 A1 | 12/2007 | Saadat |
| 2007/0287889 A1 | 12/2007 | Mohr |
| 2007/0293724 A1 | 12/2007 | Saadat et al. |
| 2008/0045842 A1 | 2/2008 | Furnish |
| 2008/0051629 A1 | 2/2008 | Sugiyama et al. |
| 2008/0132835 A1 | 6/2008 | Nagamatsu et al. |
| 2008/0161645 A1 | 7/2008 | Goldwasser et al. |
| 2008/0188868 A1 | 8/2008 | Weitzner et al. |
| 2008/0228209 A1 | 9/2008 | Demello et al. |
| 2008/0249534 A1 | 10/2008 | Gruber et al. |
| 2008/0269557 A1 | 10/2008 | Marescaux et al. |
| 2008/0269559 A1 | 10/2008 | Miyamoto et al. |
| 2008/0275300 A1 | 11/2008 | Rothe et al. |
| 2008/0300454 A1 | 12/2008 | Goto |
| 2009/0018500 A1 | 1/2009 | Carter et al. |
| 2009/0030369 A1 | 1/2009 | Nagamatsu et al. |
| 2009/0149716 A1 | 6/2009 | Diao et al. |
| 2009/0156996 A1 | 6/2009 | Milsom et al. |
| 2009/0287046 A1 | 11/2009 | Yamatani |
| 2009/0312645 A1 | 12/2009 | Weitzner et al. |
| 2010/0010296 A1 | 1/2010 | Piskun |
| 2010/0049137 A1 | 2/2010 | Fischer, Jr. |
| 2010/0106240 A1* | 4/2010 | Duggal ............ A61B 17/12022 623/1.15 |
| 2010/0152590 A1 | 6/2010 | Moore et al. |
| 2011/0065985 A1 | 3/2011 | Wehrheim |
| 2011/0077498 A1 | 3/2011 | McDaniel |
| 2011/0160538 A1 | 6/2011 | Ravikumar et al. |
| 2011/0172491 A1 | 7/2011 | Piskun et al. |
| 2011/0224494 A1* | 9/2011 | Piskun ...................... A61B 1/32 600/205 |
| 2011/0245858 A1 | 10/2011 | Milsom et al. |
| 2011/0264125 A1* | 10/2011 | Wilson ................... A61B 90/02 606/159 |
| 2011/0306832 A1 | 12/2011 | Bassan et al. |
| 2012/0083797 A1 | 4/2012 | Cabrera et al. |
| 2012/0095498 A1 | 4/2012 | Stefanchik et al. |
| 2012/0109178 A1 | 5/2012 | Edwards et al. |
| 2012/0165604 A1 | 6/2012 | Stokes et al. |
| 2013/0090527 A1 | 4/2013 | Axon |
| 2013/0144118 A1* | 6/2013 | Piskun .................. A61B 1/0051 600/104 |
| 2013/0172828 A1 | 7/2013 | Kappel et al. |
| 2013/0274553 A1* | 10/2013 | Piskun ................... A61B 1/018 600/114 |
| 2013/0317303 A1 | 11/2013 | Deshmukh et al. |
| 2013/0324795 A1 | 12/2013 | Nakajima et al. |
| 2013/0345511 A1* | 12/2013 | Piskun ............... A61B 17/0218 600/114 |
| 2014/0142393 A1* | 5/2014 | Piskun ................... A61M 39/22 600/206 |
| 2014/0316379 A1 | 10/2014 | Sonderegger et al. |
| 2015/0150436 A1 | 6/2015 | Cornhill et al. |
| 2015/0157192 A1* | 6/2015 | Piskun ............... A61B 1/00066 600/114 |
| 2015/0209024 A1* | 7/2015 | Piskun ................... A61B 1/018 600/104 |
| 2015/0265268 A1 | 9/2015 | Diao et al. |
| 2015/0265818 A1* | 9/2015 | Piskun ............... A61B 1/00082 606/192 |
| 2015/0272564 A1 | 10/2015 | Piskun et al. |
| 2015/0351890 A1 | 12/2015 | Levin et al. |
| 2016/0038172 A1 | 2/2016 | Cox |
| 2016/0081702 A1 | 3/2016 | Kan et al. |
| 2016/0106466 A1 | 4/2016 | Gruber et al. |
| 2016/0157843 A1 | 6/2016 | Dickson et al. |
| 2016/0374658 A1* | 12/2016 | Piskun ............... A61B 1/00066 600/204 |
| 2017/0079636 A1* | 3/2017 | Piskun .................. A61M 39/22 |

FOREIGN PATENT DOCUMENTS

| | | |
|---|---|---|
| CN | 102695541 A | 9/2012 |
| EP | 0163502 A2 | 12/1985 |
| EP | 1588670 A1 | 10/2005 |
| EP | 2512577 A2 | 10/2012 |
| GB | 2365340 A | 2/2002 |
| JP | S63292935 A | 11/1988 |
| JP | H08317928 A | 12/1996 |
| JP | H08336538 A | 12/1996 |
| JP | 2533732 Y2 | 4/1997 |
| JP | H1028691 A | 2/1998 |
| JP | 2000166936 A | 6/2000 |
| JP | 2000325303 A | 11/2000 |
| JP | 2001527429 A | 12/2001 |
| JP | 2004154485 A | 6/2004 |
| JP | 2004529708 A | 9/2004 |
| JP | 2005046274 A | 2/2005 |
| JP | 2007511247 A | 5/2007 |
| JP | 2008528239 A | 7/2008 |
| JP | 2008536552 A | 9/2008 |
| JP | 2009523054 A | 6/2009 |
| JP | 2009279406 A | 12/2009 |
| JP | 2010511440 A | 4/2010 |
| JP | 2011072782 A | 4/2011 |
| JP | 2012075908 A | 4/2012 |
| JP | 2013514827 A | 5/2013 |
| JP | 2015525109 A | 9/2015 |
| WO | 9101773 A1 | 2/1991 |
| WO | 96035469 A | 11/1996 |
| WO | 9640347 A1 | 12/1996 |
| WO | 03000139 A1 | 1/2003 |
| WO | 2004103430 A2 | 12/2004 |
| WO | 2006110275 A2 | 10/2006 |
| WO | 2007081601 A2 | 7/2007 |
| WO | 2008011163 A2 | 1/2008 |
| WO | 2009059296 A1 | 5/2009 |
| WO | 2009076176 A1 | 6/2009 |
| WO | 2009117696 A1 | 9/2009 |
| WO | 2011084616 A2 | 7/2011 |
| WO | 2012068048 A1 | 5/2012 |
| WO | 2012114569 A1 | 8/2012 |
| WO | 2013050880 A2 | 4/2013 |
| WO | 2013192116 A1 | 12/2013 |
| WO | 2014200737 A1 | 12/2014 |
| WO | 2015026968 A1 | 2/2015 |
| WO | 2015191125 A1 | 12/2015 |

OTHER PUBLICATIONS

International Search Report and Written Opinion for application No. PCT/US2014/040429, dated Aug. 1, 2014, 11 pages.

European Search Report dated Apr. 7, 2011 for European Patent Application No. 06789411.3, 5 pages.

Written Opinion for International Application No. PCT/US06/30464, dated Jun. 20, 2007, 5 pages.

Communication for European Patent Application No. 14733912.1, dated Jun. 11, 2018, 2 pages.

International Search Report and Written Opinion for International Application No. PCT/US18/21779, dated Jun. 14, 2018, 10 pages.

International Search Report and Written Opinion dated (Dec. 14, 2017), for PCT/US2017/050685 (16 pages).

International Search Report and Written Opinion for PCT/US10/60802, dated Aug. 24, 2011, 12 pages.

International Search Report and Written Opinion for International Application No. PCT/US2016/031355, dated Sep. 23, 2016, 17 pages.

International Search Report and Written Opinion for International Application No. PCT/US18/14388, dated Jun. 19, 2018, 9 pages.

International Search Report and Written Opinion dated (May 9, 2018), for PCT/US17/68991 (13 pages).

(56) References Cited

OTHER PUBLICATIONS

*Sergey Kantsevoy* vs. *LumenR LLC*, Answer, Affirmative Defenses and Counterclaims, Civil Action No. 17-cv-359 (ELH), filed Feb. 28, 2017, 25 pages. (See, p. 2, para. 10; p. 4, paras. 18-19; p. 11, paras. 7-8; p. 13, para. 14; p. 14, paras. 15-16.).
*Sergey Kantsevoy* v. *LumenR LLC*, Dr. Sergey Kantsevoy's Answer to LumenR LLC's Counterclaims, Civil Action No. 17-359 (ELH), filed Mar. 17, 2017, 8 pages. (See, p. 2, paras. 10, 16.).
Letter from Kurt W. Lockwood, Esq., Kacvinsky Daisak Bluni pllc, to Philip G. Hampton, II, Haynes and Boone, LLP, dated Nov. 9, 2018, 16 pages. (Entire document.).
Letter from Philip G. Hampton, II at Haynes and Boone, LLP to Kurt W. Lockwood, Esq. Kacvinsky Daisak Blun PLLC, dated Nov. 16, 2018, 2 pages. (Entire document.).
*Sergey Kantsevoy* vs. *LumenR LLC*, Complaint, Civil Action No. 17-359 (ELH), filed Feb. 7, 2017, 18 pages. (See, p. 4, paras. 10-11; p. 6, paras. 14-16; p. 7, paras. 17-19; p. 19, para. 20; p. 10, para. 28; p. 13, para. 43; p. 14, para. 49; p. 16, para. 59.).
Letter from Jeffrey M. Chamberlain, Esq., Kacvinsky Daisak Bluni pllc to Michael J. Rye, Esq., Cantor Colburn, LLP, dated Nov. 13, 2018, 3 pages. (Entire document).
Letter from Michael J. Rye, Esq., Cantor Colburn LLP to Jeffrey M. Chamberlain, Esq., Kacvinsky Daisak Bluni pllc, dated Aug. 28, 2018, 2 pages. (Entire document).
Letter from Michael J. Rye, Esq., Cantor Colburn LLP to Michael Mahoney, CEO at Boston Scientific Corporation, dated Oct. 17, 2017, 3 pages. (Entire document).
*Oleg Shikhman*, v. *Bobcat Endoscopy, LLC et al.*, Complaint, filed Oct. 17, 2017, Judicial District of Fairfield at Bridgeport, 25 pages. (See p. 3, para. 9; p. 6, para. 20; p. 16, para. 77; p. 17, para. 83; p. 18, para. 86; p. 19, paras. 92-93; p. 20, para. 99).
*Oleg Shikhman* v. *Bobcat Endoscopy, LLC et al.*, Reply to Affirmative Defenses, Matters in Avoidance and Answer to Counterclaims, dated Dec. 12, 2018, 19 pages. (See p. 9, para. 6; p. 10, paras. 9-10; p. 11, para. 13; p. 12, paras. 14, 17; p. 13, para. 19; p. 15, para. 42; p. 17, paras. 1-3.).
*Oleg Shikhman* v. *Bobcat Endoscopy, LLC et al.*, Answer, Special Defenses and Counterclaims, dated Sep. 13, 2018, 23 pages. (See p. 11, paras. 6, 8; p. 12, paras. 9-13; p. 13, paras. 14-18; p. 14, para. 19-21; p. 15, paras. 24-26; p. 16, paras. 28-29; p. 17, paras. 31-34; p. 18, paras. 35-38; p. 19, paras. 41-43; p. 20, paras. 48-49.).
*Oleg Shikhman* v. *Bobcat Endoscopy, LLC et al.*, First Amended Answer, Affirmative Defenses and Counterclaims, dated Nov. 9, 2018, 24 pages. (See p. 5, para. 53; p. 12, paras. 6-9; p. 13, paras. 10-14; p. 14, lines 15-18; p. 15, paras. 19-21; p. 16, paras. 24-26; p. 17, paras. 28-31; p. 18,paras. 33-36; p. 19, paras. 37-40; p. 20, paras. 41-44; p. 21, paras. 48-49; p. 22, para. d.).
*Oleg Shikhman* v. *Bobcat Endscopy LLC, et al.*, Memorandum of Decision, filed Oct. 31, 2019, 22 pages. (p. 1, line 15-p. 2, line 3; p. 2, lines 7-8, p. 7, lines 4-6; p. 8, lines 3-13; p. 10, line 4-p. 11, line 9; p. 18, line 5-p. 19, line 2; p. 18. footnote 15.).
"*Oleg Shikhman* vs. *Bobcat Endoscopy, LLC (F/K/A/ LumenR LLC) and Gregory Piskun, M.D. Complaint*", filed on Oct. 17, 2017, at Judicial District of Fairfield at Bridgeport, 25 pages.
"*Oleg Shikhman* vs. *Bobcat Endoscopy, LLC (F/K/A/ LumenR LLC) and Gregory Piskun, M.D. Reply to Affirmative Defenses, Matters in Avoidance and Answer to Counterclaims*", dated Dec. 12, 2018, 19 pages.
"*Oleg Shikhman* vs. *Bobcat Endoscopy, LLC (F/K/a/ LumenR LLC) and Gregory Piskun, M.D., Answer, Special Defenses and Counterclaims*", dated Sep. 13, 2018, 23 pages.
"*Oleg Shikhman* vs. *Bobcat Endoscopy, LLC (F/K/A/ LumenR LLC) and Gregory Piskun, M.D., First Amended Answer, Affirmative Defenses and Counterclaims*", dated Nov. 9, 2018, 24 pages.
"Letter from Jeffrey M. Chamberlain, Senior Principal at Kacvinsky Daisak Bluni pllc to Michael J. Rye, Esq. c/o Cantor Colburn, LLP", dated Nov. 13, 2018, 3 pages.
"Letter from Michael J. Rye, Partner at Cantor Colburn LLP to Michael Mahoney, CEO at Boston Scientific Corporation", dated Oct. 17, 2017, 3 pages.
Letter from Michael J. Rye, Partner at Cantor Colburn LLP to Jeffrey M. Chamberlain at Kacvinsky Daisak Bluni Pllc, dated Aug. 28, 2018, 2 pages.
"*Sergey Kantsevoy* vs. *LumenR LLC, Answer, Affirmative Defenses and Counterclaims*", Civil. Action No. 17-cv-359 (ELH), filed Feb. 28, 2017, 25 pages.
"Letter from Kurt W. Lockwood, Principal at Kacvinsky Daisak Bluni pllc, to Philip G. Hampton, II c/o Haynes and Boone, LLP" dated Nov. 9, 2018, 16 pages.
"Letter from Philip G. Hampton, II at Haynes and Boone, LLP to Kurt W. Lockwood, Esq. at Kacvinsky Daisak Bluni PLLC", dated Nov. 16, 2018, 2 pages.
"*Sergey Kantsevoy* v. *LumenR LLC Complaint*, Civil Action No. 17-359", filed Feb. 7, 2017, 18 pages.
"*Sergey Kantsevoy* v. *LumenR LLC, Dr. Sergey Kantsevoy's Answer to LumenR LLC's Counterclaims*", Civil Action No. 17-359 (ELH), filed Mar. 17, 2017, 8 pages.

\* cited by examiner

SYSTEM FOR A MINIMALLY-INVASIVE TREATMENT WITHIN A BODY LUMEN

CROSS REFERENCE TO RELATED APPLICATIONS

The present application claims the benefit of priority under 35 U.S.C § 119 to U.S. Provisional Patent Application Ser. No. 62/440,502, filed on Dec. 30, 2016, which is incorporated by reference in its entirety for all purposes.

BACKGROUND

Field of the Invention

This application relates to minimally invasive devices for operatively treating tissue and more specifically to minimally invasive devices which expand the body lumen to increase the working space for maneuverability of endoscopic instruments.

Description of the Related Art

Endoscopic procedures involving the gastrointestinal system offer advantages over conventional surgery in that they are less invasive and may provide visualization.

It is advantageous to provide minimally-invasive expansion of a stable, working space to expand and/or reconfigure (reshape) the working space. Such expanded, stable and optimally configured working space allows the instruments and endoscope to be independently manipulated and properly visualized around the target tissue.

It is also advantageous to provide endoscopic technology for organizing the endoscope, instruments, and working space in a manner that can maximize the working space for treatment. The larger working space can improve the ability to manipulate the instruments and endoscope in a minimally-invasive manner from outside the body. It is advantageous to have a working space that has tips of the instruments as far as practical from the target tissue to improve the maneuverability of the instruments and provide additional flexibility in approaching and visualizing the target tissue, perhaps providing more operating room for selecting a trajectory of the instruments toward the target tissue that is, for example, at least substantially perpendicular to the plane of dissection of the target tissue.

SUMMARY

The systems disclosed herein provide improved methods and devices for minimally invasively treating tissue, such as gastrointestinal tissue. The systems, for example, include a reversibly-expandable member or retractor that expands, preferably in an asymmetric manner, to maximize space for endoscopic tools(s), and in some embodiments an endoscope, to each be maneuvered independently from outside the patient to visualize a target tissue and treat the target tissue in a minimally invasive manner. Embodiments taught herein provide, among other improvements, an increase in distance between tool ports/tools and the target tissue to improve maneuverability and triangulation of the tools with respect to the target tissue, as well as a larger field of view.

In accordance with one aspect of the present invention, a system for endoscopic surgery within a body lumen of a patient is provided comprising a flexible catheter having a proximal portion, a distal portion, an expandable region at the distal portion, and an access opening. The expandable region is expandable from a collapsed insertion configuration to an expanded configuration to provide an expanded chamber on a first side of the catheter, the expandable region expanding asymmetrically and having an increased transverse dimension. The access opening is positioned on a second side opposite the first side to provide a window to access target tissue. The catheter includes a lumen dimensioned to receive an endoscopic instrument therethrough such that a distal end of the endoscopic instrument is positionable within the expanded chamber and angled laterally within the expanded chamber to access the target tissue through the window, the lumen having an opening at a distal end communicating with the chamber. The catheter is further dimensioned to receive a visualization device to visualize tissue, the endoscopic instrument received in the lumen of the catheter is movable independently of the visualization device.

In some embodiments, the catheter includes an elongated actuation member for expanding the expandable region and an actuator at the proximal portion of the catheter to move the elongated actuation member. The system can further include the visualization device with a distal end positioned adjacent a proximal region of the expanded chamber. In some embodiments, the catheter has a seal at a distal end and the visualization device is movable through the seal to visualize distally of the catheter.

In some embodiments, the window is axially aligned with the expanded chamber. The catheter in some embodiments can include an articulation member for angling a distal portion of the catheter with respect to a longitudinal axis of the catheter. In some embodiments, the expandable region includes a wall of the catheter expandable by an elongated member. In other embodiments, the expandable region is formed by an expandable balloon. The expandable balloon can have a U-shape forming a space within the U.

In some embodiments, the system includes an endoscopic instrument having a first curve extending in a first direction and a second curve extending in an opposite direction, the first curve angling away from the window and the second curve angling toward the window. The system can further include a first flexible guide positionable within the lumen of the catheter, the first flexible guide having a distal portion extendable into the chamber and the endoscopic instrument is insertable through the flexible guide. In some embodiments, at least a portion of the flexible guide is embedded in a wall of the catheter.

In accordance with another aspect of the present invention, a flexible catheter for endoscopic surgery within a body lumen of a patient is provided comprising a proximal portion and a distal portion having an expandable region expandable from a collapsed insertion configuration to an expanded configuration to provide an expanded chamber on a first side of the catheter, the expandable region expanding asymmetrically and having an increased transverse dimension. The catheter has an opening on a second side opposite the first side to provide access to target tissue, the opening being aligned with the expandable region. The catheter includes a lumen having a distal opening communicating with the expanded chamber.

In some embodiments, the expandable region is formed by an inflatable balloon. In some embodiments, the balloon has U-shaped cross-sectional configuration. The catheter can include a seal at its distalmost end. In some embodiments, the distal opening of the lumen is positioned proximal of the window; in other embodiments it is aligned with a proximal end of the window. In some embodiments, an elongated member positioned within the endoscopic device is axially movable to expand the expandable portion of the device.

In accordance with another aspect of the present invention, a method of minimally invasively treating tissue is providing comprising the steps of a) inserting into a body lumen of a patient an endoscopic device having a window and an expandable portion in a collapsed configuration, the expandable portion having an inner wall; b) after insertion of the endoscopic device into the patient, expanding the expandable portion from the collapsed configuration to an expanded configuration to create a chamber of increased transverse dimension to increase a distance between the inner wall of the expandable portion and the window; c) inserting a distal portion of a working instrument into the chamber, the working instrument extending through a first channel in the endoscopic device, and the distal portion of the working instrument extending laterally with respect to a longitudinal axis of the endoscopic device; d) visualizing the distal portion of the working instrument by a visualization device; and e) inserting a tip of the working instrument through the window to access target tissue.

In some embodiments, the step of expanding the expandable portion expands the expandable portion to only one side of the longitudinal axis of the endoscopic instrument and retracts tissue opposite the target tissue. In some embodiments, the step of expanding the expandable portion includes a step of expanding a balloon; in other embodiments, the step of expanding the expandable portion includes a step of axially moving an elongated member positioned in the endoscopic device.

DETAILED DESCRIPTION

Figure 1:
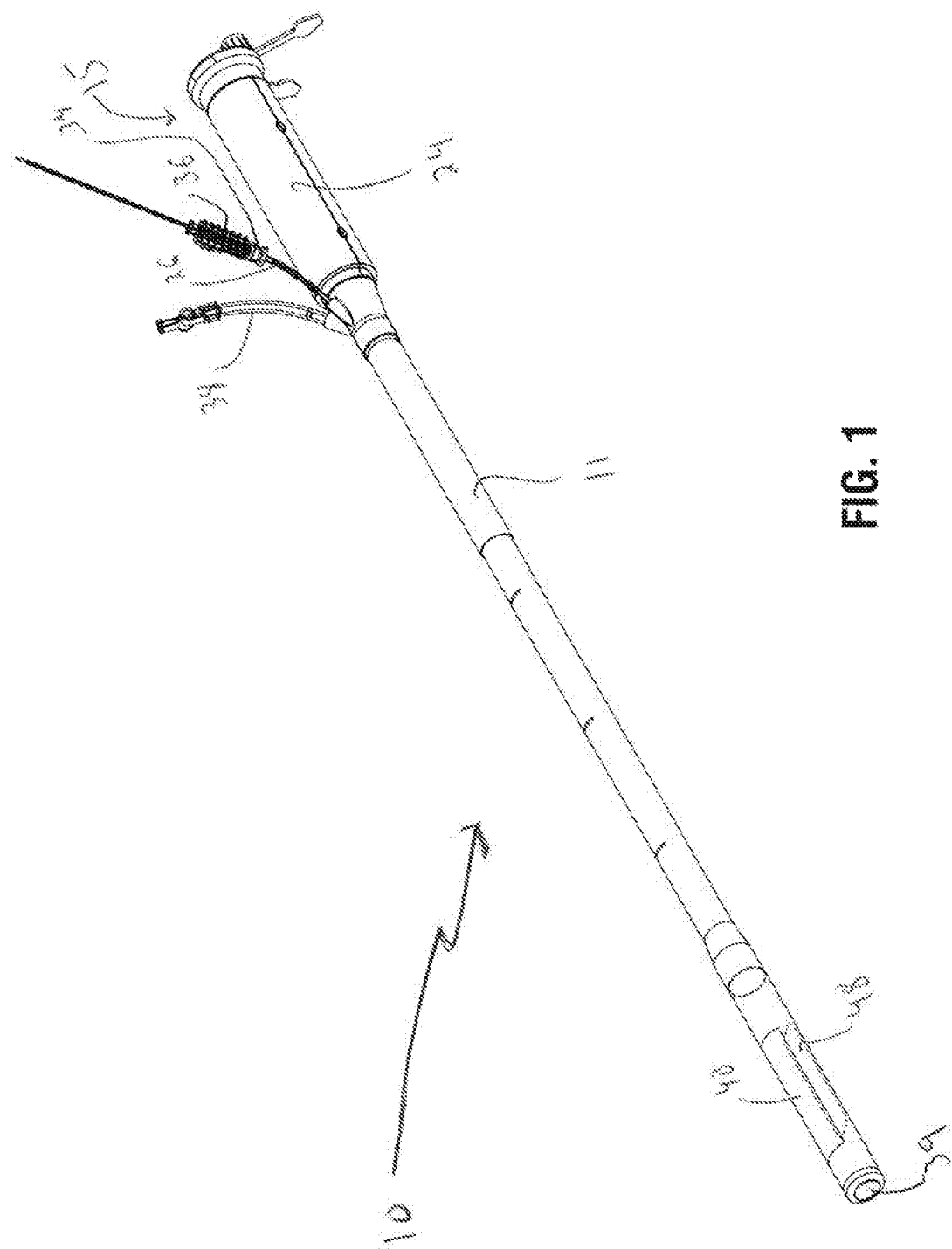
FIG. 1 is a perspective view of a first embodiment of the system of the present disclosure showing the balloon of the catheter in the non-expanded insertion position.

The disclosure is directed to improved systems, methods and devices for operatively treating disorders, such as gastrointestinal disorders, in a minimally-invasive manner. The systems can include a reversibly-expandable expandable portion or retractor that expands, preferably asymmetrically to maximize space for endoscopic tools, and an endoscope to each be maneuvered from outside the patient independently to visualize a target tissue and treat the target tissue in a minimally invasive manner. The systems include a window opposite the expandable portion or expandable member (or retractor) to provide access to the target tissue. Expansion of the expandable portion thus moves the wall of the tissue lumen further away from the window to increase the working space. The systems disclosed herein advantageously increase a distance between tips of the endoscopic tools (instruments) and the target tissue to enhance the independent maneuverability and triangulation of the tools with respect to the target tissue. This increase in distance can also provide a way of obtaining a larger field of view. The systems taught herein, for example, can (i) enable a working space to be dynamically configured in tortuous body lumens and orifices such as the gastrointestinal tract using controls from outside the body; (ii) provide a flexible, passageway for multiple surgical tools and instruments, such as an endoscope and graspers to be passed from outside the body towards the target tissue; (iii) organize and/or constrain tools in the working space; (iv) at least substantially immobilize and/or stabilize tissue; and/or (v) enable control over the position and orientation of the instruments such as the grasper in the working space from outside the body.

In some embodiments, an articulating endoscope is inserted through a channel of the catheter; in other embodiments the system is backloaded over a flexible endoscope, such as a conventional colonoscope, then the endoscope is inserted to a position adjacent the target tissue and then the catheter is advanced over the flexible endoscope so the expandable portion of the catheter is aligned with or adjacent the target tissue.

In some embodiments, the endoscopic working instruments (tools) for treating the target tissue are inserted directly through a respective lumen or channel of the multi-lumen catheter. In these embodiments, the working instruments can have a curve or double curve at a distal end which automatically assumes the curved position when exposed from the catheter so it can initially curve away from the target tissue, e.g., away from the access window, and then curve back toward the target tissue, or alternatively, the working instruments can have a mechanism actively controlled by the user to articulate/angle the distal tip to form the curved or double curved shape. In other embodiments, instead of the endoscopic working instruments (tools) being inserted directly into the lumen or channel of the catheter, a flexible tube (also referred to herein as a flexible guide or tool channel) is inserted through the lumen or channel of the catheter and acts as a guide for the endoscopic working instrument. That is, the flexible guide (tool channel) is first inserted into the lumen or channel of the catheter and then the endoscopic working instrument is inserted through the respective flexible guide. The flexible guides (tubes) can have a curve or double curve at a distal end which automatically assumes the curved position when exposed from the catheter so it can initially curve away from the target tissue, e.g., away from the access window and then curve back toward the target tissue, or alternatively, the flexible tubes can have a mechanism actively controlled by the user to articulate/angle the distal tip of the flexible tubes to form the curved or double curved shape. In these embodiments utilizing the flexible tubes, the curving and maneuverability of the flexible tubes controls the positioning and orientation of the endoscopic instruments, and therefore the endoscopic instruments need not be provided with a pre-curved tip or bending mechanisms, although optionally they can have a pre-bent (pre-curved) tip. The tool channels can be substantially straight when in the insertion position within the confines of the multi-lumen tube (catheter) and return to the pre-bent position when exposed from the confines of the catheter. In other embodiments, the tool channels terminate at the distal opening of the catheter and the working instruments have the curved tips.

In preferred embodiments, the systems disclosed herein include an expandable portion (region) or member which creates an expanded working space within the body lumen. More particularly, when working in a confined body lumen, such as the colon, expansion of the lumen is limited because it is undesirable to over-expand which could stretch the lumen beyond its ability to return to its normal state or more dangerously could rupture the lumen. The asymmetric working spaces disclosed herein are designed to expand, reconfigure and/or reshape the body lumen—transform the cylindrical space within the body lumen to a non-cylindrical asymmetrical space (i.e., change the geometry) to shift the space to create more working space and distance for instrument access to the target tissue to provide both visual and mechanical improvements. Stated another way, in a cylindrical working space, there is a lot of area of unused space while in the reshaping embodiments disclosed herein, the space is moved or shifted to reduce the unused space and create a larger area for tissue access and treatment.

The systems disclosed herein also enable triangulation to be achieved. Tissue triangulation, wherein the tissue is triangulated between two endoscopic instruments, enhances access and maneuverability.

The tools inserted directly through the catheter lumen or through the flexible guide can be any type of endoscopic tool including for example, a grasper, a forceps, a snare, a scissor, a knife, a dissector, a clamp, an endoscopic stapler, a tissue loop, a clip applier, a suture-delivering instrument, or an energy-based tissue coagulator or cutter.

Although two tool channels are illustrated, it should also be appreciated that a system with more than two tool channels or with only one tool channel can also be utilized. Additionally, the endoscope can have a working channel for insertion of one or more working instruments such as a grasper or dissector. The endoscope is shown in use as terminating adjacent the opening in the catheter at a proximal end of the expanded chamber, however, it is also contemplated that the endoscope can be inserted into the chamber and manipulated and/or articulated within the chamber.

In addition to creating the working space with the above advantages, the working space is formed to create an increased working distance for the tools for treatment, e.g., polyp dissection, to enhance maneuvering and manipulating the individual tools, and enabling tissue triangulation. Working space distance is also advantageously increased to enhance visibility of the target tissue.

This increased maneuverability can improve the view of the lesion and ability to manipulate and dissect the lesion. For example, a grasper can be advanced out of the instrument channel into the working space and flexed towards the polyp, then actuated to grasp the polyp and retract the tissue to expose the base of the polyp for dissection by a dissection tool through the multi-channel systems taught herein.

The systems provided herein can be used in several different methods of treatment. For example, the systems can be used in a method of treating a gastrointestinal lesion. The lesion can include, for example, a perforation, a tissue pathology a polyp, a tumor, a cancerous tissue, a bleed, a diverticuli, an ulcer, an abnormal vessel, or an appendix.

In some embodiments, the window is closable to capture and isolate the removed target tissue during removal of the catheter from the subject. This is advantageous if the dissected tissue may be a cancerous or it is otherwise desirable to contain it during removal of the catheter from the body lumen.

Figure 5:
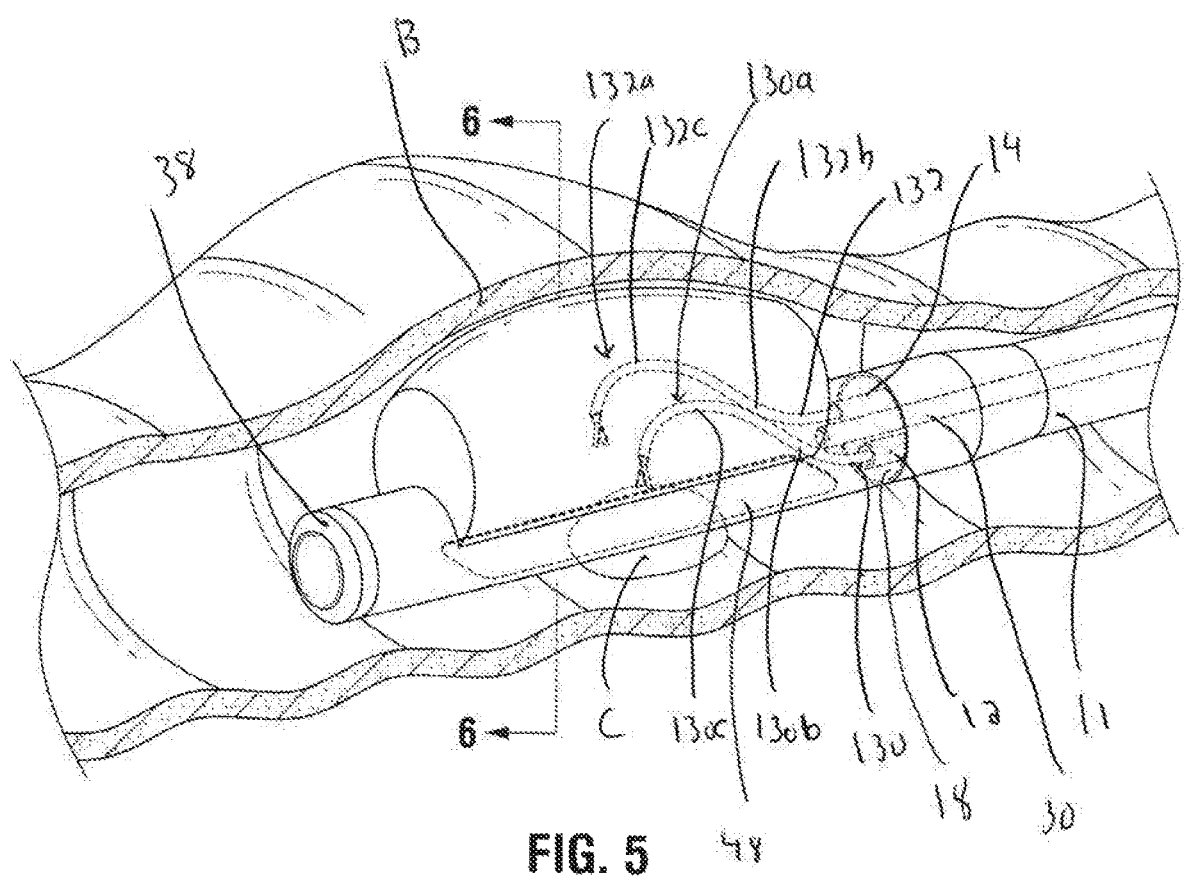
FIG. 5 is a view similar to FIG. 4C showing insertion of two endoscopic instruments into the chamber (space) created by the expanded balloon.
Figure 6:
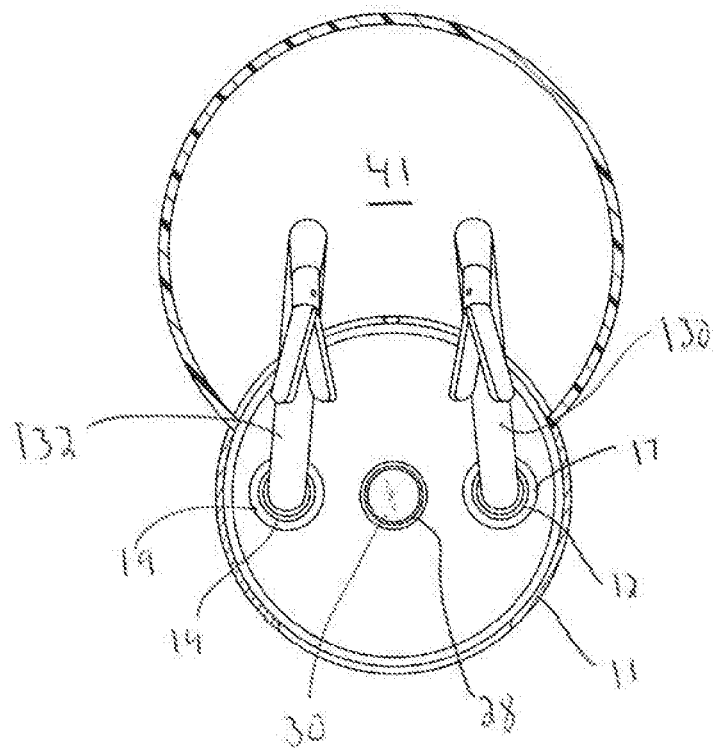
FIG. 6 is a transverse cross-sectional view taken along line 6-6 of FIG. 5.

Turning now to the drawings, wherein like reference numerals identify the same parts or components, FIG. 1 illustrates a first embodiment of the system, designated generally by reference numeral 10. System 10 includes a flexible catheter or tubular member 11 configured to receive one or more tool channels or flexible instrument guides. FIG. 5 shows two tool channels 12, 14, it being understood that in some embodiments, only one tool channel can be utilized and in other embodiments more than two tool channels can be utilized. The catheter 11 can have multiple lumens to receive the tool channels. The tool channels 12, 14 can be packaged as a kit with the catheter 11 or alternatively, the tool channels 12, 14 can be packaged separately. In other embodiments, the tool channels are packaged already inside the lumens of the catheter 11. Each tool channel 12, 14 has a lumen (channel) extending from a proximal to a distal end to receive an endoscopic instrument (tool) therethrough. Note in alternate embodiments, the endoscopic instruments can be inserted directly through the catheter instead of through tool channels, as discussed in more detail below.

The tool channels 12, 14 (also referred to herein as flexible tubes or flexible guides) are inserted through the proximal end 15 of the catheter 11 and advanced through respective lumens 17, 19 in the catheter 11. The lumens provide communication with the expanded chamber of the catheter and have distal openings proximate the chamber. The catheter 11 can include ports at a proximal end, cooperating with the tool channels 12, 14, which can include valves to maintain insufflation when the tool channels 12, 14 are inserted therethrough and translated axially therein. The tool channels 12, 14 can have a pre-bent curve as shown for example in the embodiment in FIG. 17 or can be of shorter length and terminate at the opening 18 of catheter 11 as in FIG. 5.

Figure 17:
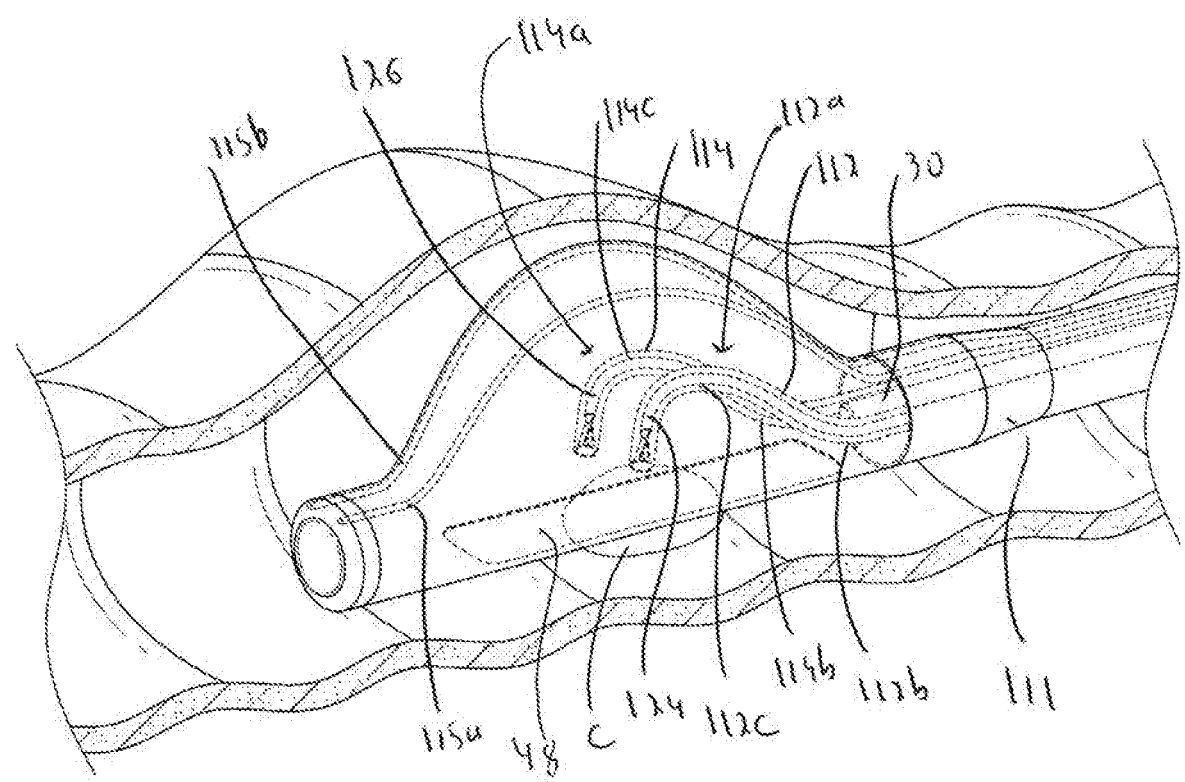
FIG. 17 is a perspective view of the distal portion of another alternate embodiment of the system showing the catheter in the expanded position and working instruments extending through the instrument guides (tool channels)
Figure 18:
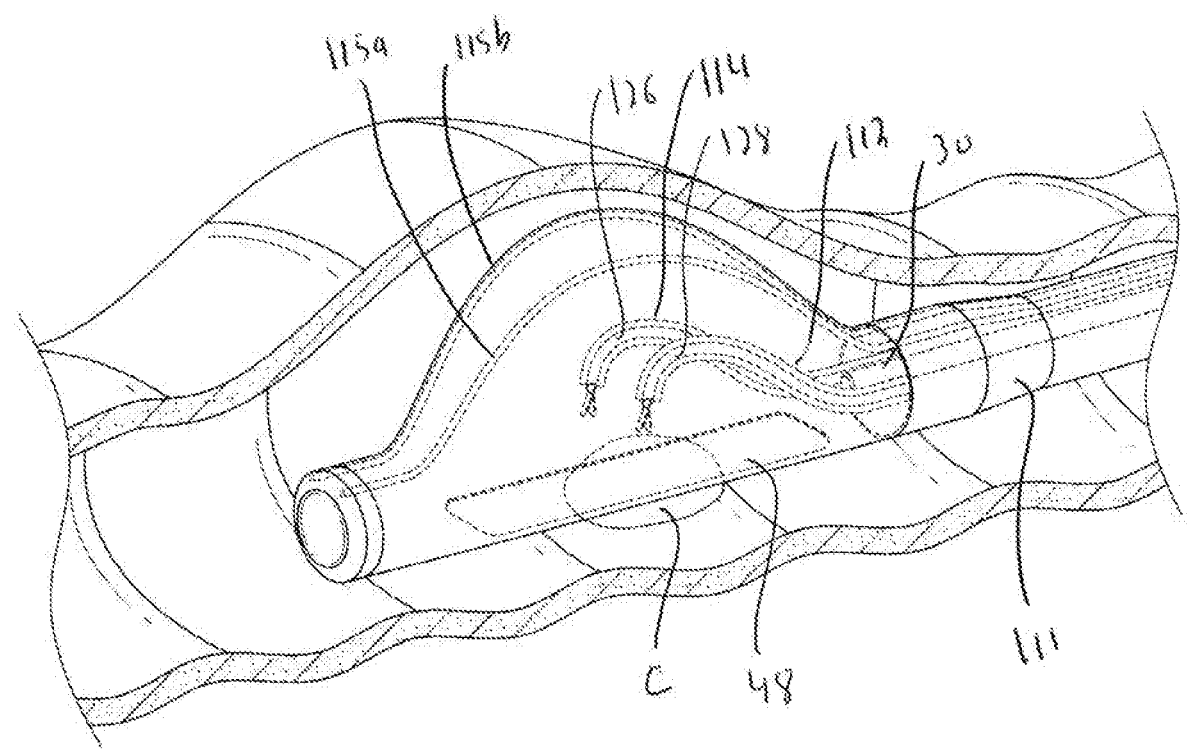
FIG. 18 is a view similar to FIG. 17 showing the endoscopic instruments advanced from the instrument guides.
Figure 19:
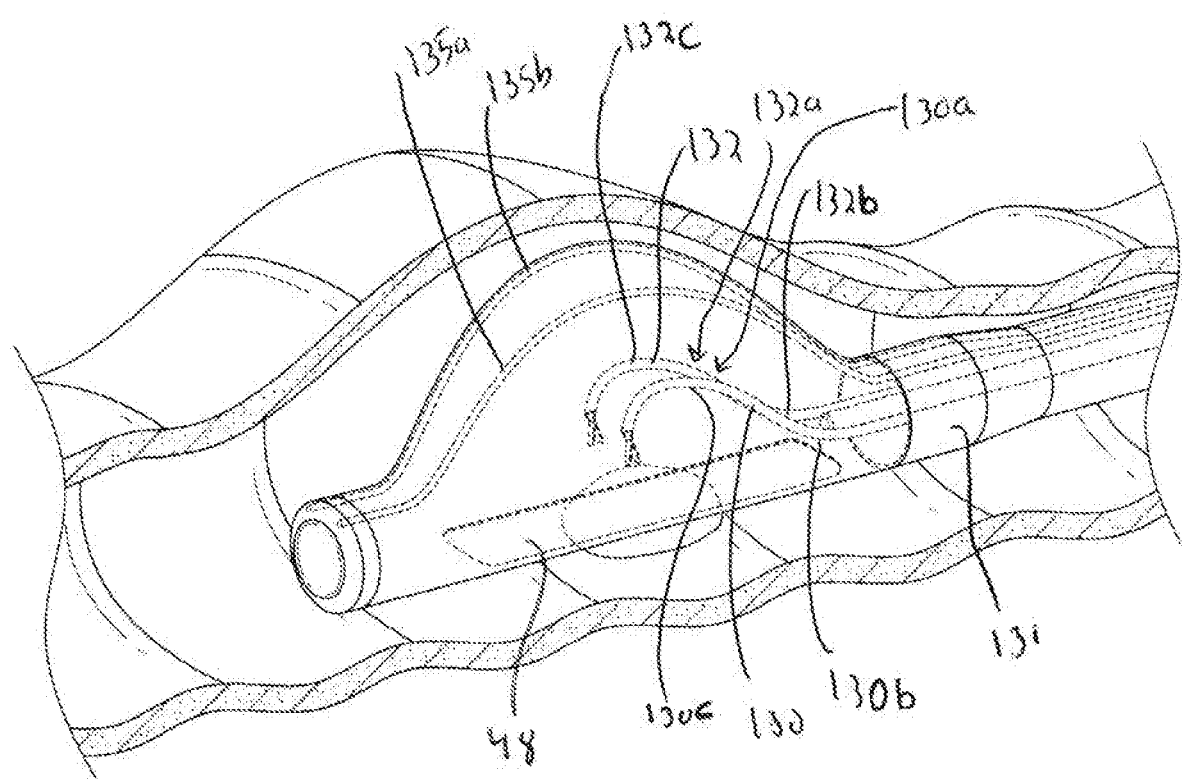
FIG. 19 is a perspective view of the distal portion of another alternate embodiment of the system showing the catheter in the expanded position and two endoscopic instruments extending into the expanded space.

In the embodiment of FIG. 17, tool channel (tube) 112 has a pre-bent tip 112a to provide a curved distal end. The pre-bend preferably takes the form of a first bend 112b extending away from the target tissue (and window 48) and transitioning to a second bend 112c extending downwardly toward the target tissue. Tool channel (tube) 114 also preferably has a pre-bent tip 114a, providing a curved distal end. The pre-bend preferably takes the form of a first bend 114b extending away from the target tissue (and window 48) and transitioning to a second bend 114c extending downwardly toward the target tissue. When the tool channels 112, 114 are inserted into the lumens of catheter 111, the tips 112a, 114a are preferably substantially straightened to facilitate advancement through the lumens. When the tool channels 112, 114 are advanced sufficiently distally so the distal tips 112a, 114a are exposed from the confines of the walls of the catheter lumens, the tips 112a, 114a, return to the pre-set curved position as shown in FIGS. 17 and 18. The endoscopic instruments (tools) 124, 126, follow the curve of the respective tool channel 112, 114 and as shown in FIG. 18, the endoscopic tools 124, 126 are advanced out the respective tool channel 112, 114 to expose the working end, e.g., the jaws, for performing the surgical procedure. Thus, since the tool channels 12, 114 have the double curve, the instruments 124, 126 need not have the double curve as they can take the shape of the tool channels 112, 114. However, alternatively, they also could have the double curve shape like the tool channels 112, 114. The tool channels 112, 114 can be composed of superelastic material, although other materials to provide the curved tip which returns from a substantially straight insertion shape to a curved shape when exposed can also be used, such as stainless steel. Also, as in the other embodiments disclosed herein, shape memory properties of material such as Nitinol can be used with a memorized curved tip shape. In alternative embodiments, the tool channels 112, 114 can have a mechanism such as a pull wire which is actuated to bend its distal end. The tool channels 112, 114 can be unattached to the catheter 111 so that the user can freely control their axial movement from a proximal end portion during use, the proximal end extending proximally of the proximal end of the catheter. However, it is also contemplated that in alternate embodiments the tool channels can be attached to the catheter. In the embodiments where the tool channel is not utilized and the instruments are inserted directly through the catheter lumens, e.g., FIG. 19, or where the tool channels are of shorter length and terminate adjacent the opening of the catheter (adjacent the proximal end of the expanded region), e.g., FIG. 5, the endoscopic instruments 130, 132 would have the first and second bends, e.g., the pre-bent distal tips 130a, 132aq would have a first bend 130b, 132b extending away from the target tissue (and window 48) and transitioning to a second bend 130c, 132c extending downwardly toward the target tissue. In the embodiment with the double bend tool channels, e.g., tool channels, 112, 114, the endoscopic instrument can rely on the double bend of the tool channels 112, 114 to form the bend of the instruments or the instrument can also have the double bend. The double bend of the tool channels and/or endoscopic instruments increases the distance from the target tissue as the instruments would first curve away from the target tissue and then bend toward the target tissue. Such increased distance improves maneuverability of the instruments and visibility. Note the double bend tool channels, the short tool channels and no tool channels can be utilized with any of the embodiments disclosed herein The tool channels 12 and 14 (and 112, 114) can optionally include markings at a region proximal to the catheter 11 (or 111) to provide a visual indicator to the user of the depth of insertion of the tool channels 12, 14 (and 112, 114) through the catheter lumens 17, 19. The tool channels 12, 14 (and 112, 114) can have a luer fitting with a valve, at the proximal end which can close off backflow of insufflation gas from the body. This maintains insufflation when the endoscopic tool is inserted through the tool channels. The tool channels in an alternate embodiment can have a hemostatic valve connected at a proximal end to maintain insufflation during tool insertion. The flexible guides described herein, e.g., flexible guides (tool channels) 112, 114, can be color coded to improve the system's usability. For example, flexible guide 112 can be of a first color, such as red, and flexible guide 114 can be of a second color, such as black. In this way, when the user is manipulating the flexible guides 112, 114 at their proximal ends outside the patient's body, the user will more readily see the corresponding color coordinated tip being manipulated within the expanded cage. Note the entire flexible guide can have the same color or alternatively the matching color can be only at the proximal end visible to the user and the distal end visible by the endoscope. It should also be appreciated that instead of color coding, other indicia can be provided so the user can match the proximal end of the flexible guide with the distal end within the chamber.

In one embodiment, the tool channels 112, 114 (and 12, 14) can be composed of a flexible soft material, such as Pebax. A superelastic nitinol backbone can in some embodiments be embedded in the wall of the Pebax material, e.g., within the curved portion. Other materials are also contemplated.

Figure 15:
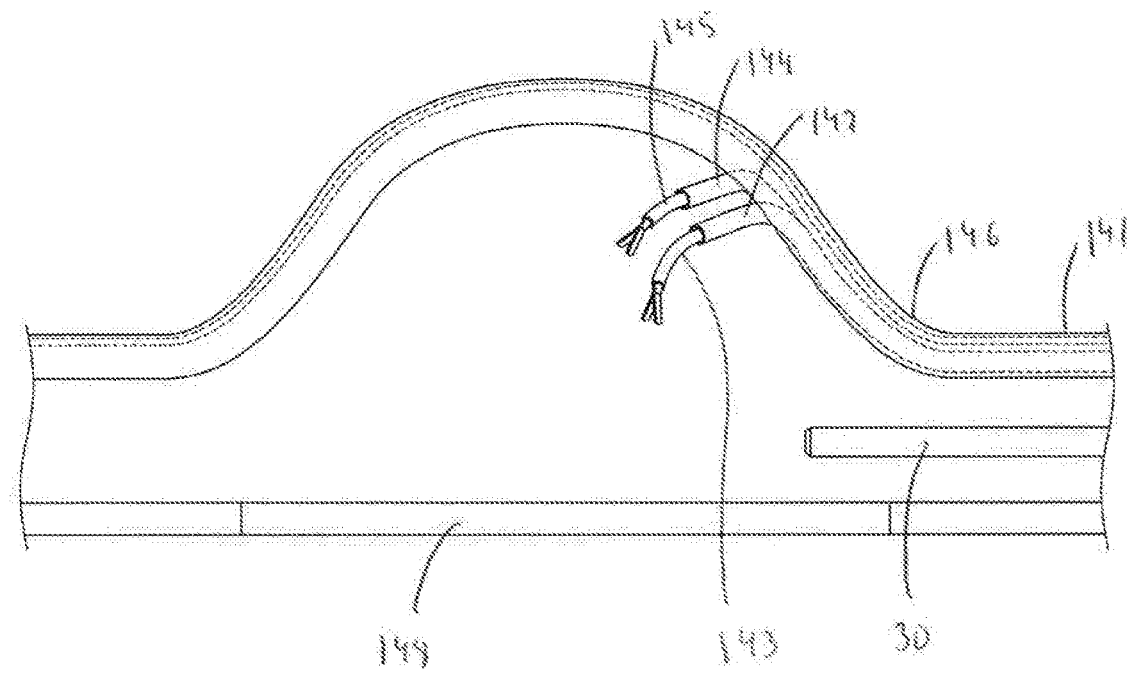
FIG. 15 is a perspective view of the distal portion of another alternate embodiment of the system showing the catheter in the expanded position.
Figure 16:
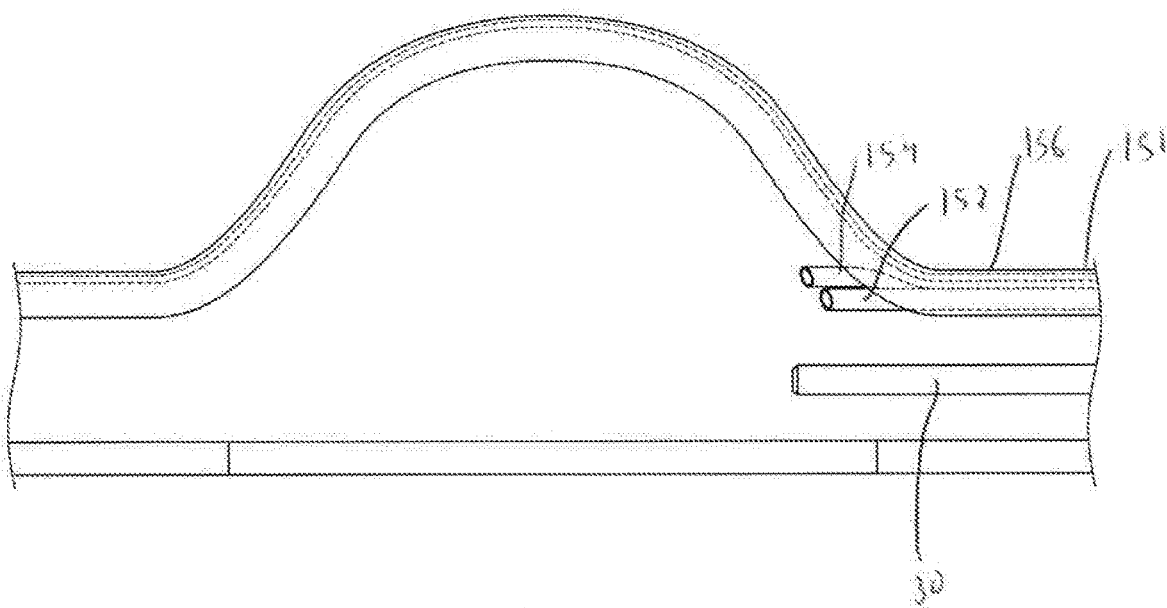
FIG. 16 is a perspective view of the distal portion of another alternate embodiment of the system showing the catheter in the expanded position.

In the foregoing embodiments, tool channels are shown extending through a lumen of the catheter. In the alternate embodiment of FIG. 15, the tool channels 142, 144 are embedded in the wall 146 of catheter 141. As shown, the tool channels 142, 144 extend within the wall 146, and move as the wall 146 of the catheter 141 is moved to an expanded configuration, following the curve of the wall 146. In this manner, when the catheter wall 146 is expanded to increase the distance from the lesion, it carries the tool channels 142, 144 a further distance from the window 148 and target tissue to provide the aforedescribed advantages for the endoscopic tools 143, 145 inserted therethrough. These tools 143, 145 can follow the bend of the tool channels or alternatively have a preformed bend. In the alternate embodiment of FIG. 16, tool channels 152, 154 are shorter channels, embedded in wall 156 of catheter 151. These tool channels 152, 154 extend out of the wall 156 proximal to the region of the wall that expands. The expandable region of the catheters 141 and 151 can be expanded in the same manner as catheter 62 of FIG. 7 described below or in the other manners described herein. Also note, in this embodiment of FIG. 16, instruments such as instruments 130, 132 of FIG. 19 having the double curve to increase the working distance from the target tissue would preferably be utilized, extending into the expanded region and passing through access window 158.

Referring back to catheter 11 of the embodiment of FIG. 1-2B, 3-6, catheter 11 also preferably has a lumen 28 configured and dimensioned to receive an endoscope 30. In some embodiments, the lumen 28 is dimensioned to receive a conventional endoscope, e.g., a conventional colonoscope, and the catheter 11 is backloaded over the endoscope. In alternate embodiments, the lumen 28 can receive an articulating endoscope. Moreover, in alternate embodiments, the endoscope can be inserted into the catheter already inserted into the body lumen.

Catheter 11 includes a handle housing 24 at the proximal portion. Catheter 11 also includes tubing 26 having a luer coupling 34 and a control switch 36 for closing off an internal gasket. Catheter 11 also has tubing 38 having a one-way stopcock to provide an insufflation port. This port can be used to supplement the insufflation gas provided by the endoscope 30. The insufflation gas flows through lumen in the area around the endoscope 30 since the cross-sectional dimension of the lumen exceeds the cross-sectional dimension of the endoscope 30 to leave a sufficient gap. Alternatively, tubing 26 can additionally or alternatively be used to inflate the expandable portion 40 of the catheter 11, or another port can be provided for injection of inflation fluid into fluid channel 42 within catheter 11 which communicates with the expandable member 40.

Figure 2A:
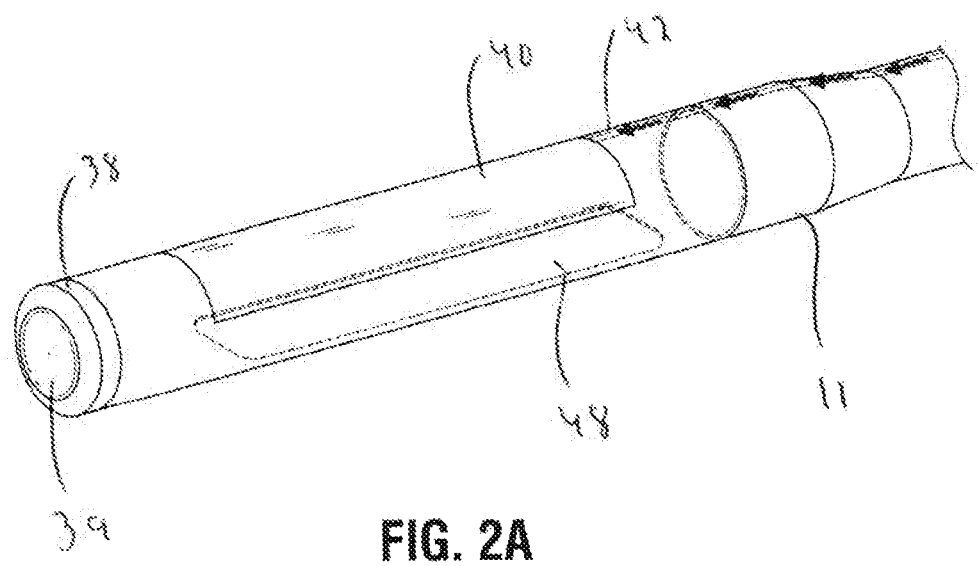
FIG. 2A is an enlarged view of the distal portion of the catheter of FIG. 1 showing the balloon in the non-expanded position.
Figure 2B:
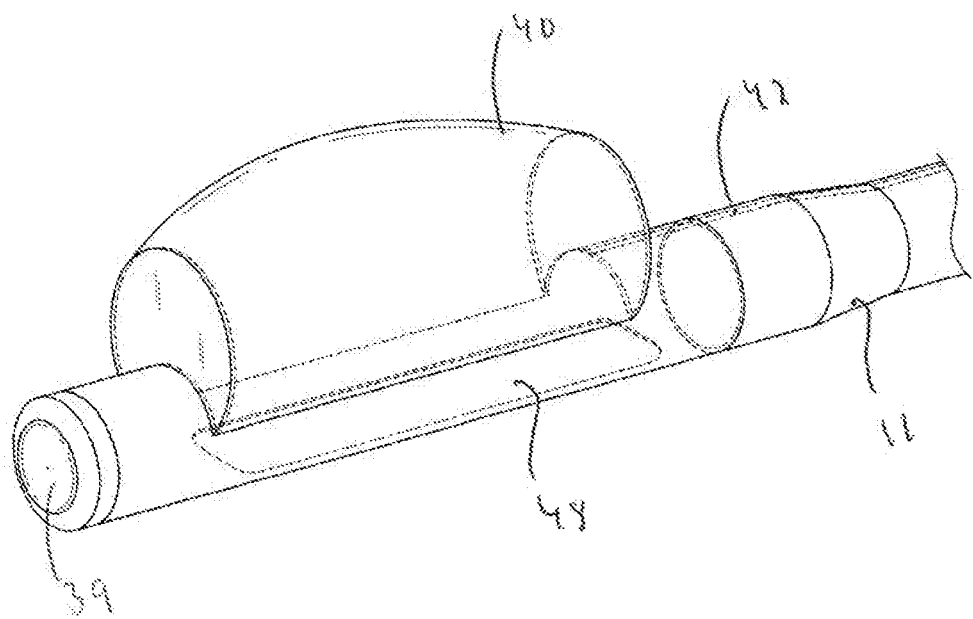
FIG. 2B is a view similar to FIG. 2A showing the balloon in the expanded position.
Figure 4A:
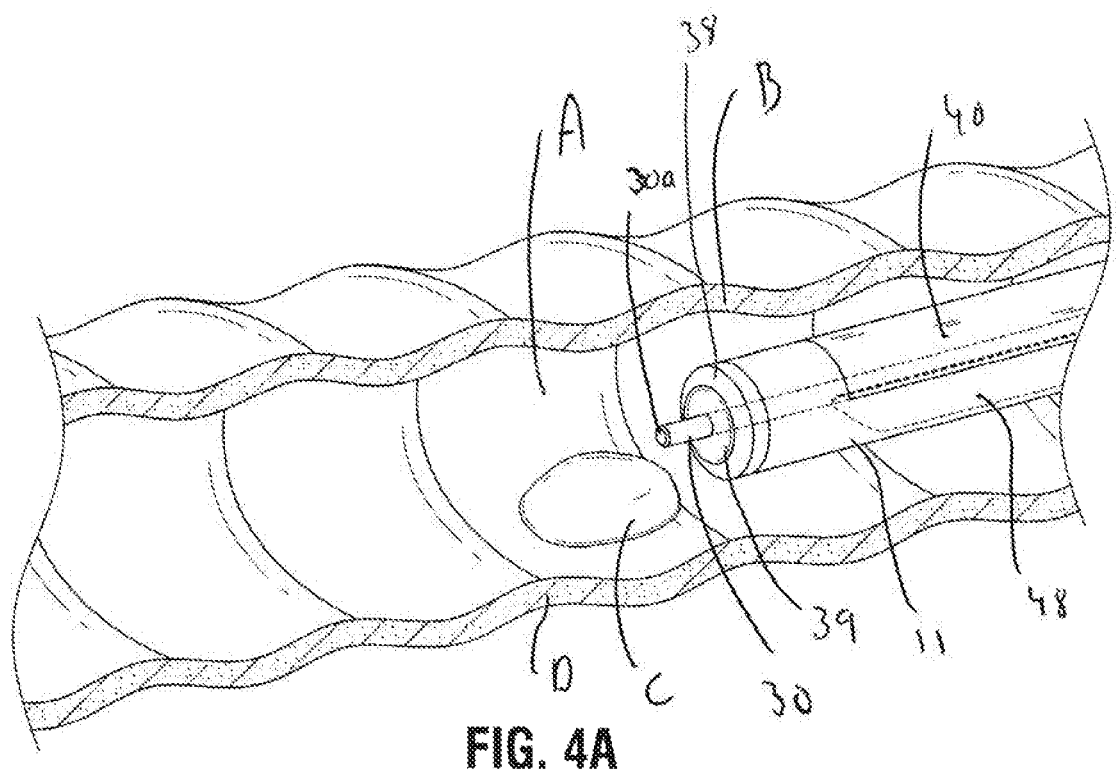
FIG. 4A is a perspective view showing the catheter of FIG. 1 partially inserted into the body lumen.
Figure 4B:
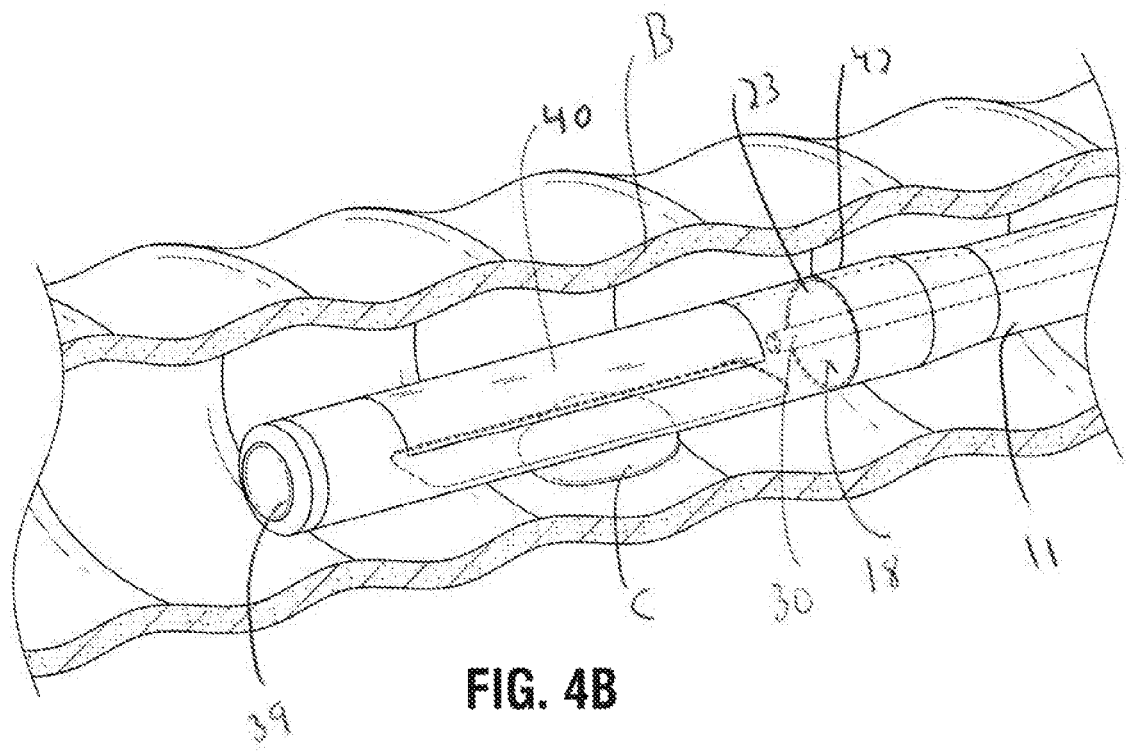
FIG. 4B is view similar to FIG. 4A showing advancement of the catheter of FIG. 1 to position the window adjacent the lesion.
Figure 4C:
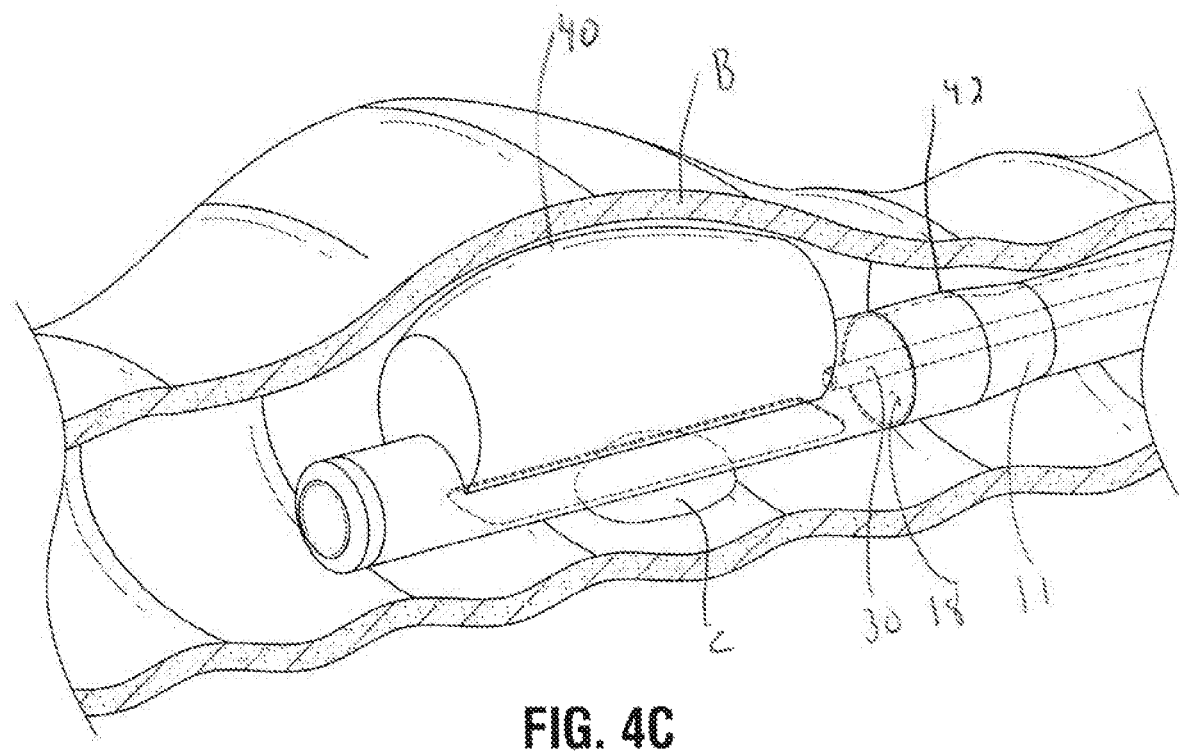
FIG. 4C is a view similar to FIG. 4B showing expansion of the balloon to provide an expanded chamber.

Expandable member or portion 40 at the distal portion of catheter 11 as shown has a reduced profile collapsed insertion position (condition or configuration) shown in FIGS. 1, 2A, and 4B, and is expandable to an expanded position (condition or configuration) of FIGS. 2B and 4C to expand the body lumen to create a chamber of increased transverse dimension upon injection of inflation fluid through channel 42 which communicates with expandable portion 40. When expanded, it moves the wall B of the body lumen A opposite the target tissue, e.g., opposite the lesion C, to expand the wall B away from the lesion C to provide an increased working space, i.e., increased space between the inner wall of the expandable portion and window. Note in the embodiment of FIG. 1, the expandable member 40 is in the form of an inflatable balloon having a U-shape so that the interior of or space within the U (FIG. 6) creates an expanded working space 41 for the working instruments, e.g., provides space for the curves of the instruments. This enables the instruments 130, 132 inserted into the space to have an increased distance from the lesion than would not otherwise be available in the absence of such expansion. Note that in a preferred embodiment, the expandable member 40 is expandable asymmetrically, i.e., to only one side of a longitudinal axis of the catheter 11, so that only the wall opposite the target tissue is moved.

Figure 2C:
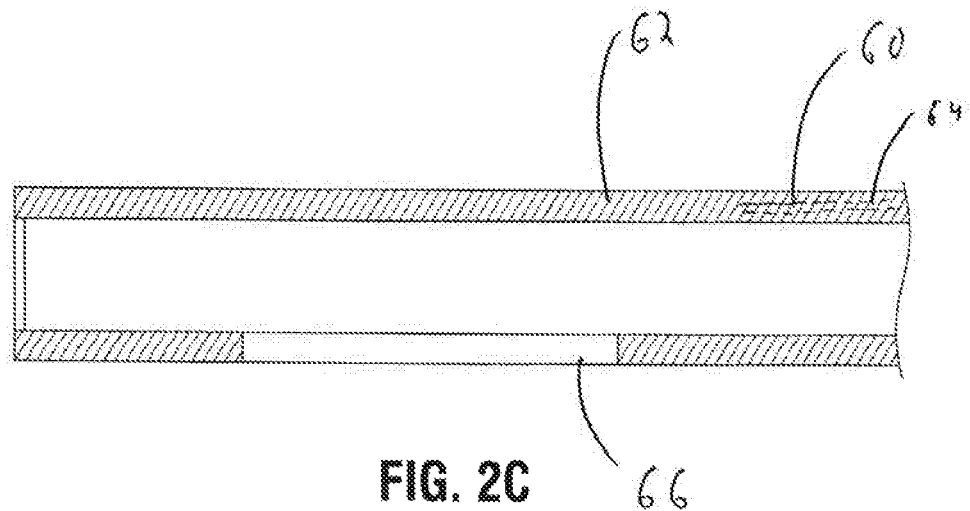
FIG. 2C is a cross sectional view of a distal portion of a catheter of an alternate embodiment showing the expandable portion in the non-expanded insertion position.
Figure 2D:
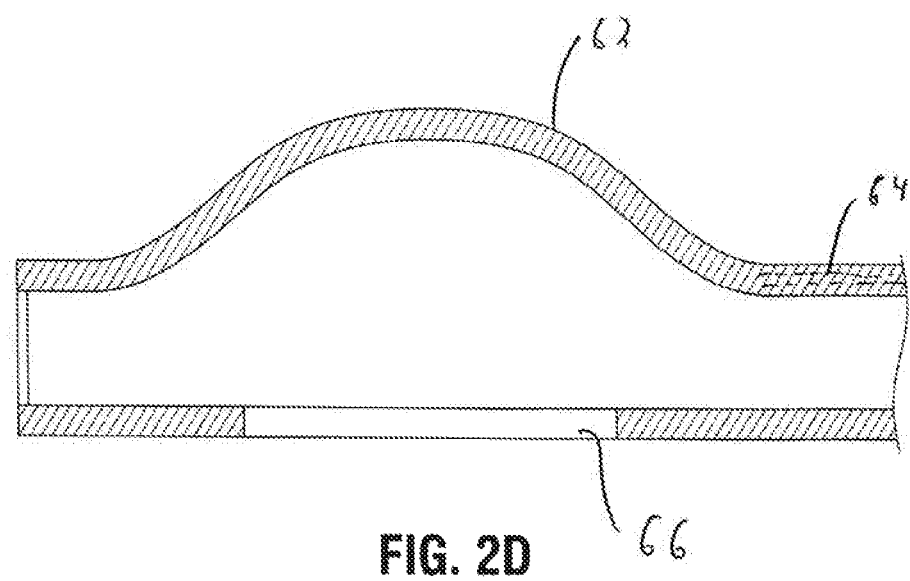
FIG. 2D is a cross sectional view similar FIG. 2C showing the expandable portion in an expanded position.
Figure 3:
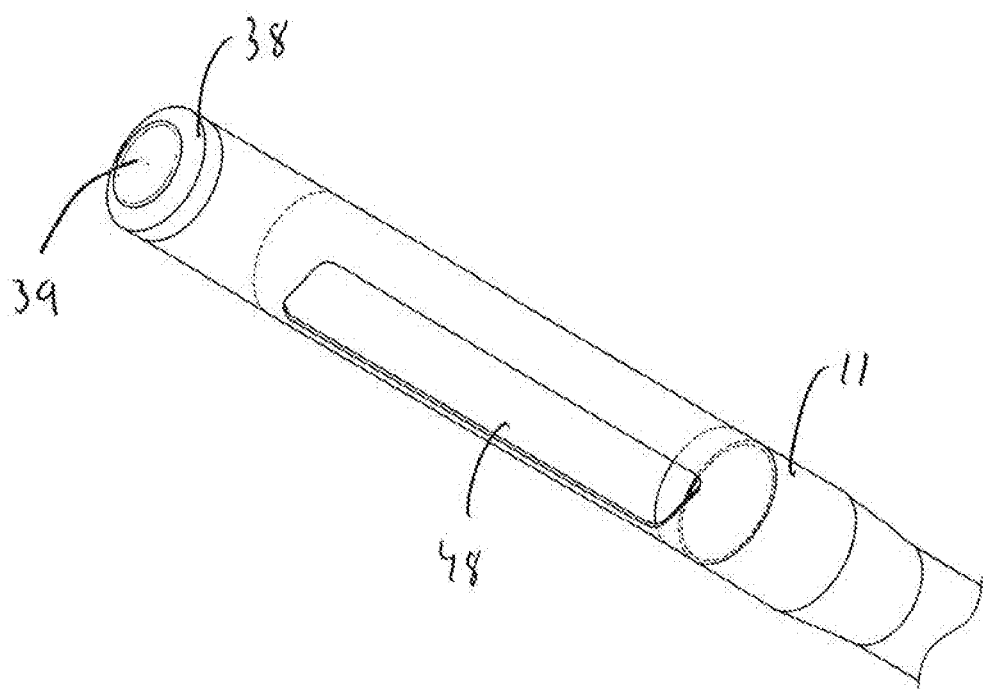
FIG. 3 is a perspective view of the distal portion of the catheter of FIG. 2A showing the opposing side of the catheter.

Although the expandable member 40 is shown in the form of an expandable balloon attached to the catheter 11 at a proximal and distal portion by known techniques, in alternate embodiments, the catheter wall itself can be formed of material that can be inflated for expansion such as shown in FIGS. 2C and 2D to form an expandable portion (retractor). Catheter 60 has a wall 62 which is inflated via fluid channel 64 extending through the wall 62 and communicates with an inflation port as described above with respect to the embodiment of FIG. 1. Such inflation moves the wall 62 from the collapsed non-expanded insertion position of FIG. 2C to the expanded position of FIG. 2D to expand the wall of the body lumen on the side opposite the access window 66 which provides access to the target tissue in the same manner as window 48 described herein. In all other respects, the catheter 60 is the same as catheter 11 and provides passage for the various embodiments of the tool channels and endoscopic instruments as described herein. Alternatively, instead of an inflatable expandable member, a mechanical expander, such as a series of flexible elements as in FIGS. 10 and 17, can be utilized for asymmetric expansion of the working space, discussed in detail below.

Opposite the expandable member 40 on the other side of the longitudinal axis of the catheter 11 is a window 48 formed in the body of the catheter 11, e.g., cutout in the body of the catheter 11, to provide access to the target lesion. The window 48 is shown axially aligned with expandable member 40. The window 48 can be of various shapes and sizes other than that shown, provided it is a large enough opening for the endoscopic instruments to access and treat the target tissue, e.g., a lesion on the wall of the body lumen, opposite the wall which is expanded by the expandable member 40. In some embodiments it can be dimensioned to enable polyps or other removed tissue to be placed inside the expanded region for encapsulation and withdrawal when the expanded region is collapsed and the catheter withdrawn from the body.

The catheter 11 includes a distal cap 38 having a membrane or a balloon like material 39 forming a seal. The endoscope 30 can be inserted through the seal 39 as shown in FIG. 4A to view the region distally of the catheter 11 during insertion. The endoscope 30 can then be retracted proximally with the seal resealing. The seal 39 restricts or occludes air flow as well as other fluid flow. Such seal can be used in any of the embodiments disclosed herein.

The use of the system 10 of FIG. 1 will now be described with reference to removing a lesion, such as a polyp, from a colon wall, it being understood, however, that the system 10 can used for other procedures within the colon or the gastrointestinal tract, as well as used for other procedures in other body lumens or body spaces of a patient.

Turning first to FIG. 4A, a distal viewing endoscope 30, in which the catheter 11 has been advanced over the proximal end thereof, or alternatively the catheter 11 has been backloaded over the distal end thereof, is inserted through lumen A in the colon in a procedure to remove the target polyp C from the wall B of the colon. The endoscope 30 in this embodiment is a distal viewing scope with a wide distal viewing area of, for example about 150-170 degree range, so the polyp C and surrounding area can be visualized. The endoscope 30 is positioned so the viewing lens (and illumination) at the distal end 30*a* extends through the seal 39, e.g., membrane 39 of distal cap 38 of catheter 11, for forward viewing distally of catheter 11, with the membrane 39 maintaining the seal. After placement of the endoscope 30 adjacent the target tissue, i.e., slightly proximal of the target polyp C, the catheter 11 is further advanced over the endoscope 30 to the position of FIG. 4A. The catheter 11 is advanced over the endoscope 30 as shown in FIG. 4B until the window (opening) 48 is aligned with the polyp C. As can be appreciated, in this insertion position of the catheter 11, the expandable member 40 is in the non-expanded (or collapsed) position. As shown, in this position, the distal end 30a of the endoscope 30 is preferably positioned at the end of distal opening 18 of catheter 11, i.e., proximal of the window 48, so as not to extend into the working space 41 created by the expandable member 40 to thereby leave more room for maneuvering of the tool channels and/or endoscopic instruments within the working space. Other positions, however, are also contemplated, e.g., in some versions the endoscope 30 can extend into the working space 41 created by the expandable member 40.

Next, the expandable member 40 is expanded, e.g., by injection of inflation fluid through channel 42, as shown in FIG. 4C, thereby creating the asymmetric working space (chamber) 41 in the interior of the balloon and gap in the catheter 11 above the window 48. Thus, the expandable member 40 expands the chamber to one side of the longitudinal axis of the catheter and retracts tissue opposite the target tissue e.g., lesion.

Next, tool channels 12, 14 are inserted through the ports in the proximal region of the catheter 11 and advanced by the user through the catheter lumens 17, 19 so they extend out the distal openings of the lumens 17, 19 and into the expanded working space (expanded chamber) 41 as shown in FIG. 5. Note in the embodiment of FIG. 5, the tool channels 12, 14 extend slightly distally of the distal opening 18 of the catheter 11 terminating proximal of window 48 (or alternatively terminating at a proximal region of the window 48) while in the embodiment of FIG. 17, as the tool channels 112, 114 emerge from the lumens of the catheter 111, and out of the confines of the lumen walls of the catheter 111, their distal tips 112a, 114a return to their curved (bent) position, curving upwardly (as viewed in the orientation of FIG. 17) away from the polyp C and then curving downwardly toward polyp C. The terms upwardly and downwardly as used herein refer to the orientation of the system in the referenced Figures—if the position of the system changes, the orientation and terms would also change. Note the tool channels 112, 114 can be independently rotated and/or moved axially to adjust their position with respect to the polyp C. Further note that in the embodiment of FIG. 19 where tool channels are not provided, this step of insertion of the tool channels is skipped and the endoscopic instruments 130, 132 are inserted directly through the catheter 131. Note in FIG. 4C, the expandable member 40 is first expanded, followed by insertion of the tool channels 12, 14 out of the catheter lumens 17, 19 and into the working space 41. However, it is also contemplated that in an alternative embodiment, the tool channels 12, 14 can be inserted through the catheter lumens 17, 19 prior to expansion of the expandable member 40.

After insertion of the tool channels 12, 14 (or 112, 114), endoscopic instruments (tools) 130, 132 are inserted through the luer fitting of the tool channels 12, 14 (or 112, 114) and advanced through the lumen (channel) of the tool channel. As shown in FIG. 5, a first endoscopic instrument 130 extends from tool channel 12 and out the distal end into the expanded working space 41 created by the expandable member 40. Similarly, a second endoscopic instrument 132 extends from tool channel 14 and out the distal end into the expanded working space 41 created by the expandable member 40. The endoscopic instruments 130, 132 assume their double curve tip shape when exposed from the tool channels. Note in the embodiment of FIGS. 17 and 18, the first endoscopic instrument 124 is inserted through the luer fitting of tool channel 112, advanced through the lumen of the tool channel 112 to follow the double curve of the tool channel 112, and extends out the distal end into the working space 41 and the second endoscopic instrument (tool) 126 is inserted through the luer fitting of tool channel 114, advanced through the lumen of the tool channel 114, to follow the double curve of the tool channel 114 and extends out the distal end into the working space. As noted above, the tool channels can include a valve, such as hemostatic valves, so insufflation is not lost during insertion and removal of the endoscopic instruments from the tool channels. The endoscopic instruments therefore extend laterally with respect to a longitudinal axis of the catheter to contact and treat tissue, e.g., remove the polyp C. As can be appreciated, once the tool channels 112, 114, are in the desired position with respect to the polyp C, they can be considered as defining a fixed curve. This means that when the endoscopic instruments are axially advanced, they move closer to the target polyp C, without a change in curvature and without a change in their axial position with respect to the polyp C, thus providing an extra degree of freedom. In some embodiments, one endoscopic instrument can be a grasper to apply tension on the polyp C while another endoscopic instrument can be an electrosurgical dissector to dissect/sever the polyp C from the colon wall B. Other endoscopic instruments for polyp removal can also be utilized. Additionally, in some embodiments, a single tool channel can be utilized and another endoscopic instrument, e.g., a grasper or a dissector, can be inserted through a working channel (lumen) of the endoscope. Such instrumentation inserted through an endoscope can also be utilized with the embodiments having two or more tool channels. Also note that due to the angles of the endoscopic instruments, tissue triangulation can be achieved.

After removal of the polyp C from the colon wall B, it is placed within the catheter 11 for removal from the body. Expandable member 40 is deflated to return the expandable member 40 to its collapsed position of FIG. 4B for removal of the catheter 11.

In some embodiments, after placement of the polyp or other structure within the catheter, the window can be closed. This is shown for example in the embodiment of FIGS. 20A and 20B which has a purse string to close the window as discussed below. Such closable window can be utilized with any of the embodiments disclosed herein.

Figure 7:
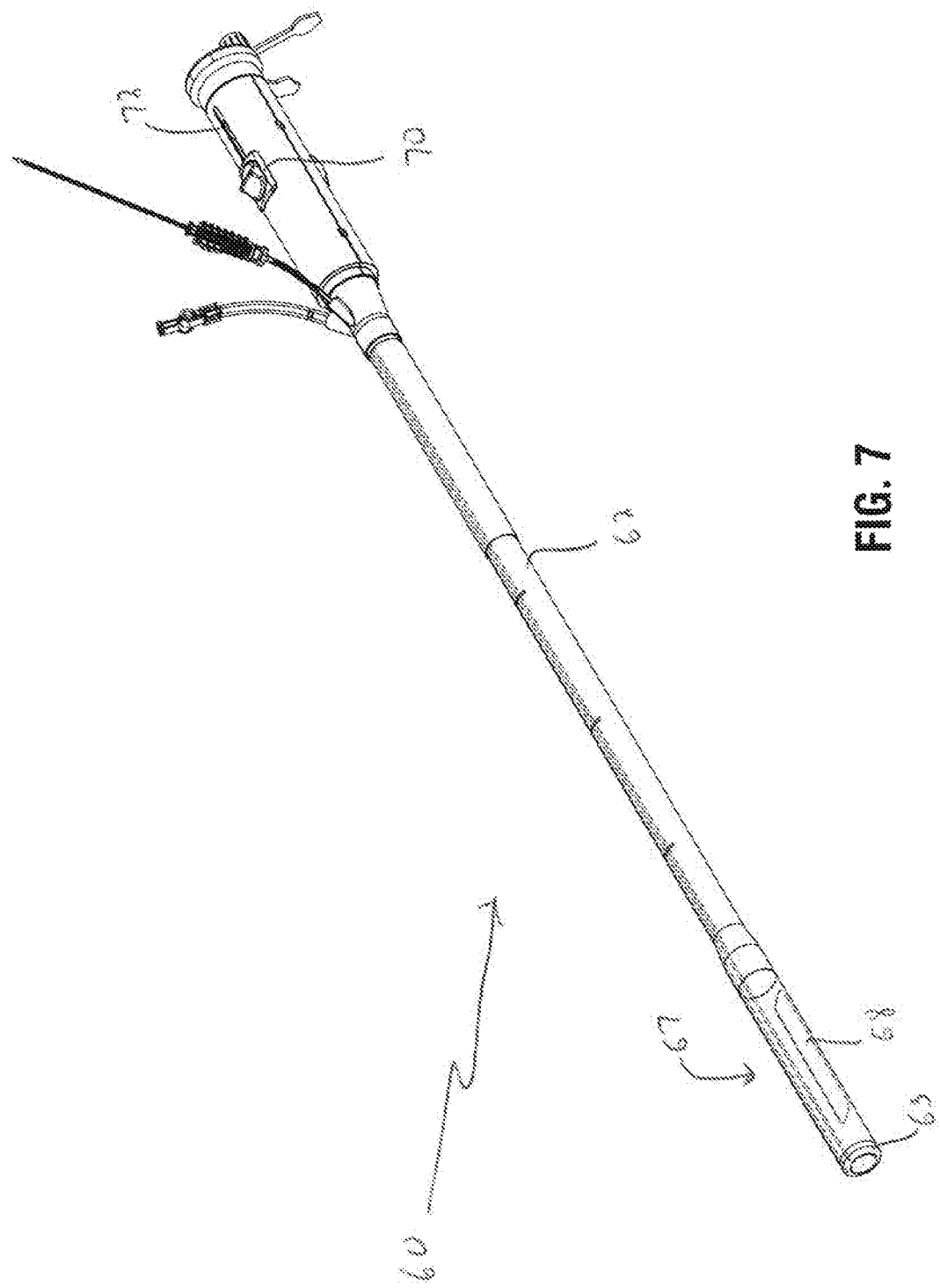
FIG. 7 is a perspective view of an alternate embodiment of the system with the catheter shown in the non-expanded insertion position.

FIGS. 7-14 show an alternate embodiment of an expandable region or portion for increasing the working space. In the embodiment of FIG. 7, the system 60 is identical to system 10 of FIG. 1 except for the expandable portion (member). More specifically, flexible catheter 62 of system 60 is identical to flexible catheter 11 except that expansion occurs via pull wires that cause bulging of a portion of the catheter. Being otherwise identical, for brevity, other features of the catheter 62 and system 60 are not discussed herein since the features and their function of system 10 and catheter 11 are fully applicable to system 60 and catheter 62. Additionally, the various embodiments of the tool channels discussed above, e.g., short tool channels such as tool channels 12, 14 and double curved tool channels such as tool channels 112, 114, can be utilized with system 60. Alternatively, the endoscopic instruments can be inserted through catheter 62 without tool channels as in the embodiment of FIG. 19. Alternatively, the endoscopic instruments discussed above, e.g., double curved instruments 130, 132 or instruments 124, 126 can be utilized with the system 60. By way of example, system 60 is shown with tool channels 12, 14 terminating adjacent distal opening 63 and endoscopic instruments 130, 132 extending therefrom.

Figure 8:
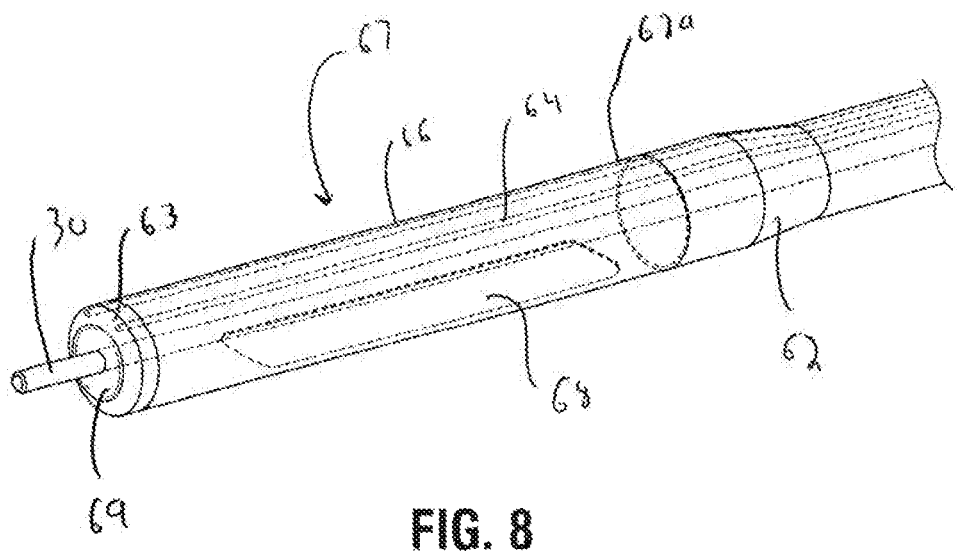
FIG. 8 is an enlarged perspective view of the distal portion of the catheter of FIG. 7 in the non-expanded position with the endoscope protruding beyond the distal end.
Figure 9:
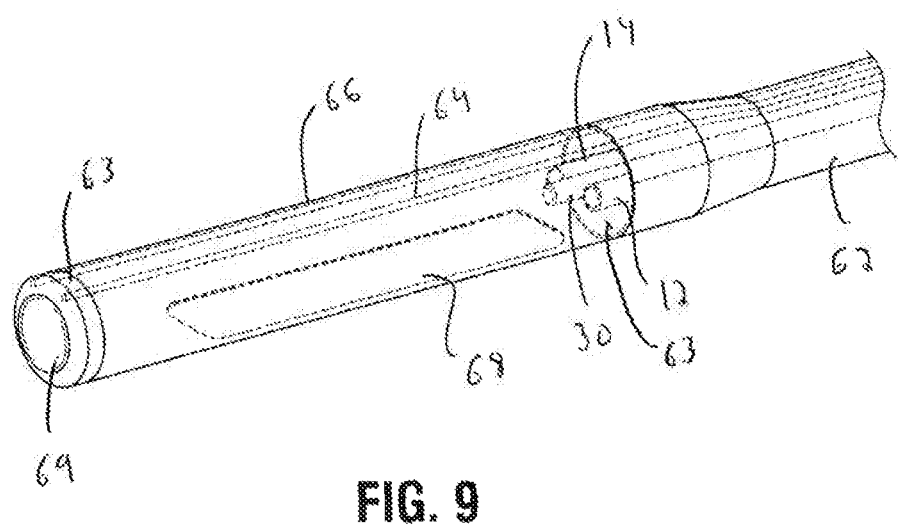
FIG. 9 is a view similar to FIG. 8 showing the endoscope retracted proximal of the window and two tool channels extending through the catheter and positioned proximal of the window.
Figure 10:
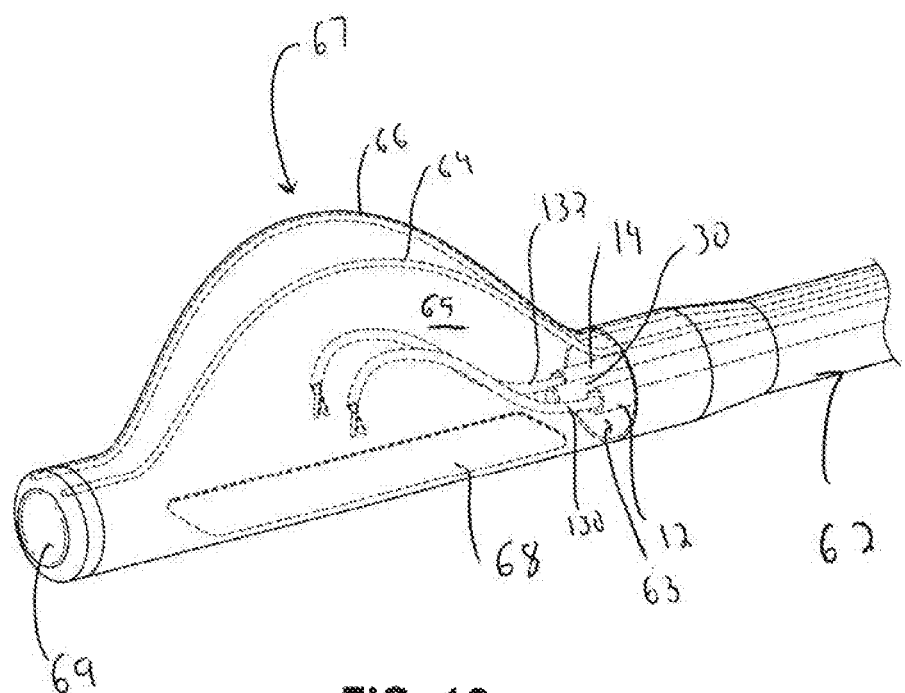
FIG. 10 is a view similar to FIG. 9 showing the catheter in the expanded position and two endoscopic instruments inserted through the tool channels into the space created by the expanded portion of the catheter.
Figure 11:
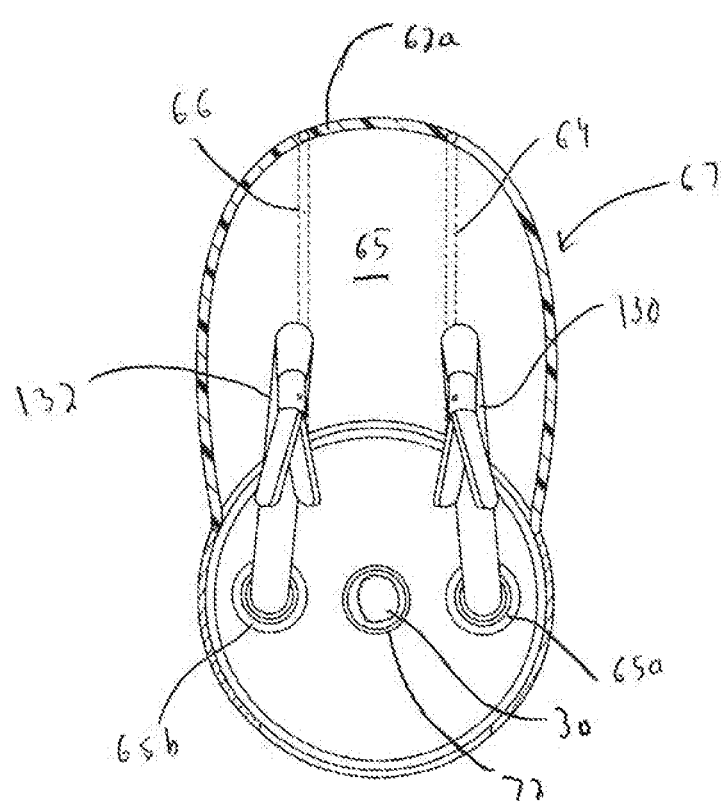
FIG. 11 is a transverse cross-sectional view of the catheter of FIG. 10 in the region of the expandable portion of the catheter.

Turning now to FIGS. 7-10, the catheter 62 has elongated actuation members in the form of a first pull wire 64 and a second pull wire 66, both embedded in wall 62a of catheter 62. The tensioning wires 64, 66 are affixed at the distal end to a distal portion or an end cap 63 of catheter 62. They are operatively connected to an actuator 70, such as a slidable actuator 70 at the proximal portion of the catheter 62 shown in FIG. 7, although other types of actuators are also contemplated. Note cables, tubes or other elongated tensioning members can be utilized instead of wires 64, 66 to effect expansion of the expandable portion of the catheter 62. Actuator 70 is operatively connected to wires 64, 66 so that as it slides proximally within the slot 72 of catheter 62, it applies tension to the wires 64, 66, pulling them axially proximally to pull back on the distal end of the catheter 62. This causes the catheter 62 at region 67 to bulge outwardly radially as shown in FIGS. 10 and 11 to create an increased working space 65 of increased transverse dimension for manipulation of endoscopic instruments, e.g., instruments 130, 132 inserted through lumens 65a, 65b of the catheter 62, within the increased working space. This asymmetric expansion, e.g., expansion to only one side of a central longitudinal axis of the catheter 62, is also shown in the transverse cross-section of FIG. 11. Note such wires are also utilized in the embodiment of FIG. 17 and labeled as wires 115a, 115b, and utilized in the embodiment of FIG. 19 and labeled as wires 135a, 135b. Note expandable region (portion) 67 of catheter 62 can have a thinner wall than other regions of the catheter or can be made of a more flexible material than other regions of the catheter to facilitate expansion (bulging) of the catheter when wires 64, 66 are pulled. It is also contemplated that the catheter can be alternatively structured so that pushing the wires causes bulging of the catheter. In such embodiments, an actuator such as actuator 70 is operatively connected to the push wires and is slid axially distally to buckle the wires (which are fixed at their distal end to the distal end or cap of the catheter), thereby causing radial outward bulging of the catheter at its expandable region.

After the procedure, e.g., removal of a polyp via access of instruments 130, 132 through window 68 positioned opposite the expanded region 67, the actuator 70 is returned to its initial position of FIG. 7 to collapse the expandable region 67 of the catheter 62 to the position of FIG. 9. Note the catheter 62, like catheter 11, can have a seal 69 like seal 39 of FIG. 1 to enable advancement of the endoscope 30 therethrough as shown in FIG. 8 for viewing distally of the catheter and then retracted to the position of FIG. 9 for viewing of the expanded region of the endoscopic instruments. The endoscope 30 can be inserted through catheter lumen 72 in the same manner as in the FIG. 1 embodiment.

Figure 12:
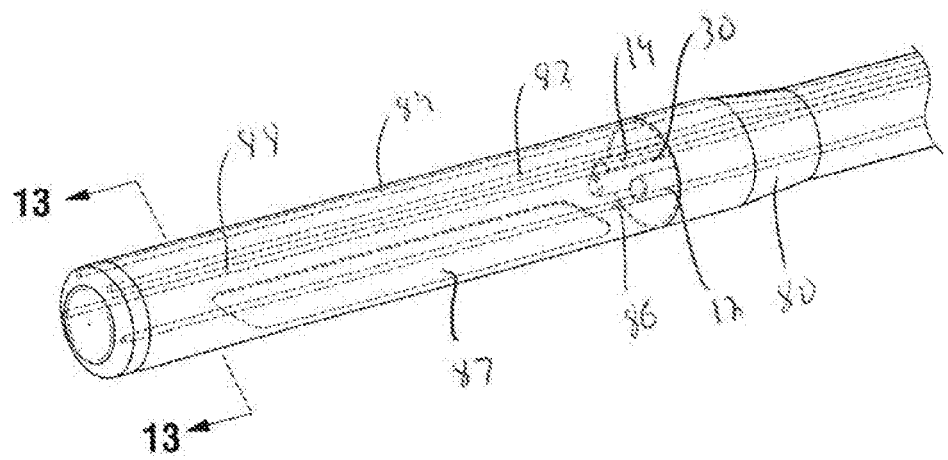
FIG. 12 is a perspective view of the distal end of another alternate embodiment of the catheter showing the catheter in the non-expanded insertion position.
Figure 13:
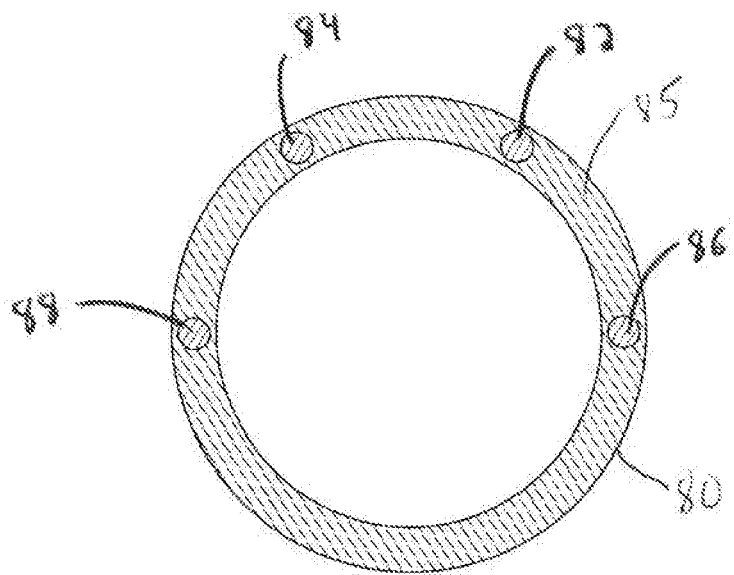
FIG. 13 is a transverse cross-sectional view taken along line 13-13 of FIG. 12.
Figure 14:
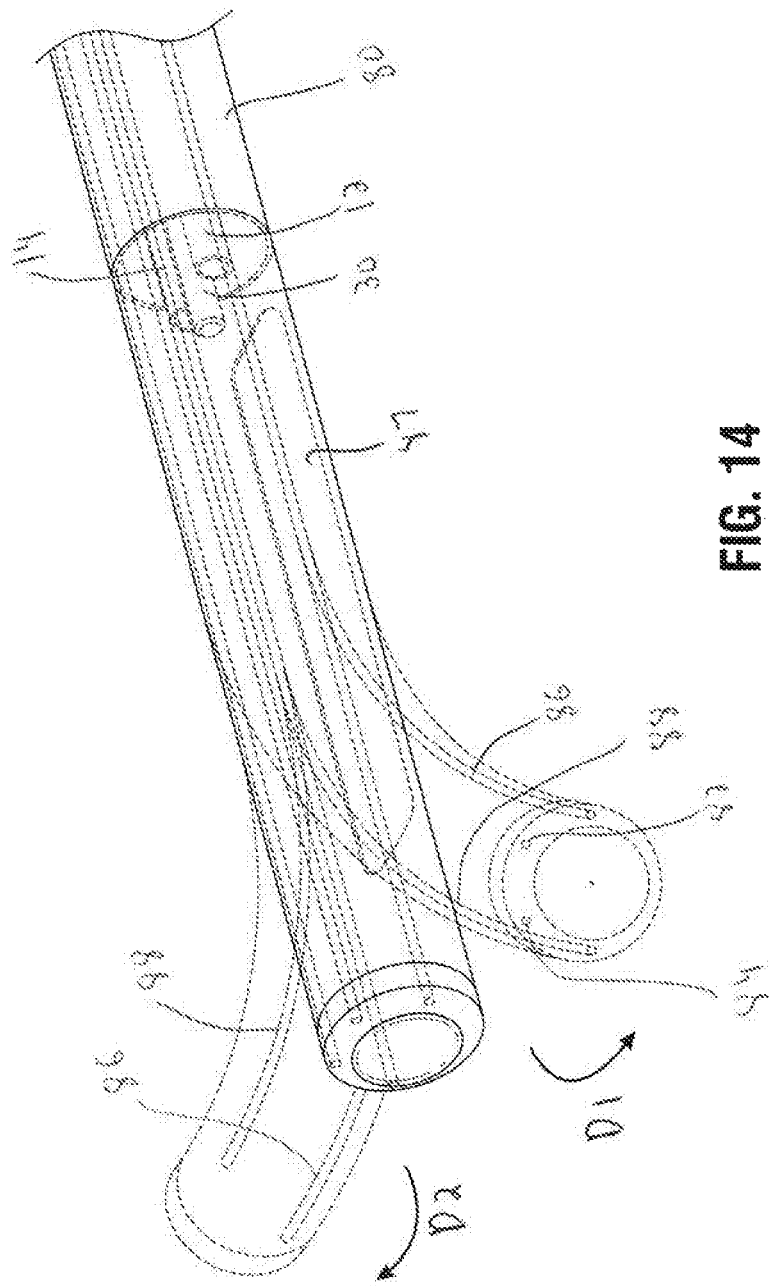
FIG. 14 is a perspective view similar to FIG. 12 showing (in phantom) the catheter articulated to two different positions.

In some embodiments, it may be advantageous to provide for articulation of the distal portion of the catheter, before expansion and/or after expansion. FIGS. 12-14 illustrate an example of a mechanism to effect articulation, and shown for use with catheter 80 similar to catheter 62 of FIGS. 7-11, although such articulation feature, either by the mechanism of FIG. 12 or an alternative articulation mechanism, can be used with any of the catheter embodiments disclosed herein. As shown, in addition to pull wires 82, 84 which are identical to pull wires 64, 66 of catheter 62, (or in addition to the aforedescribed push wires), the catheter 80 includes two articulation members 86, 88 embedded in the catheter wall 85 on opposite sides of the catheter and spaced from pull wires 82, 84. The articulation members 86, 88 can be in the form of elongated wires as shown, or alternatively in the form of other elongated members such as cables or tubes. To articulate the distal portion of catheter 80 in a first direction, e.g., direction D1 of FIG. 14, articulation wire 86 is pulled proximally; to articulate the distal portion of catheter 80 in a second direction, e.g., direction D2 of FIG. 14 opposite to direction D1, articulation wire 88 is pulled proximally. Movement or wires 86, 88 back to their original position returns the catheter to the non-articulated straighter position. Such articulation improves the positioning of the expandable region of the system. In all other respects, catheter 80 is identical to catheter 62, e.g., window 87 is identical to window 68 to provide instrument access to tissue. In an alternate embodiment, a pair of wires can effect both expansion of the expandable region, e.g., by pushing a pair of wires, and articulation by pulling of select one of the wires.

Figure 20A:
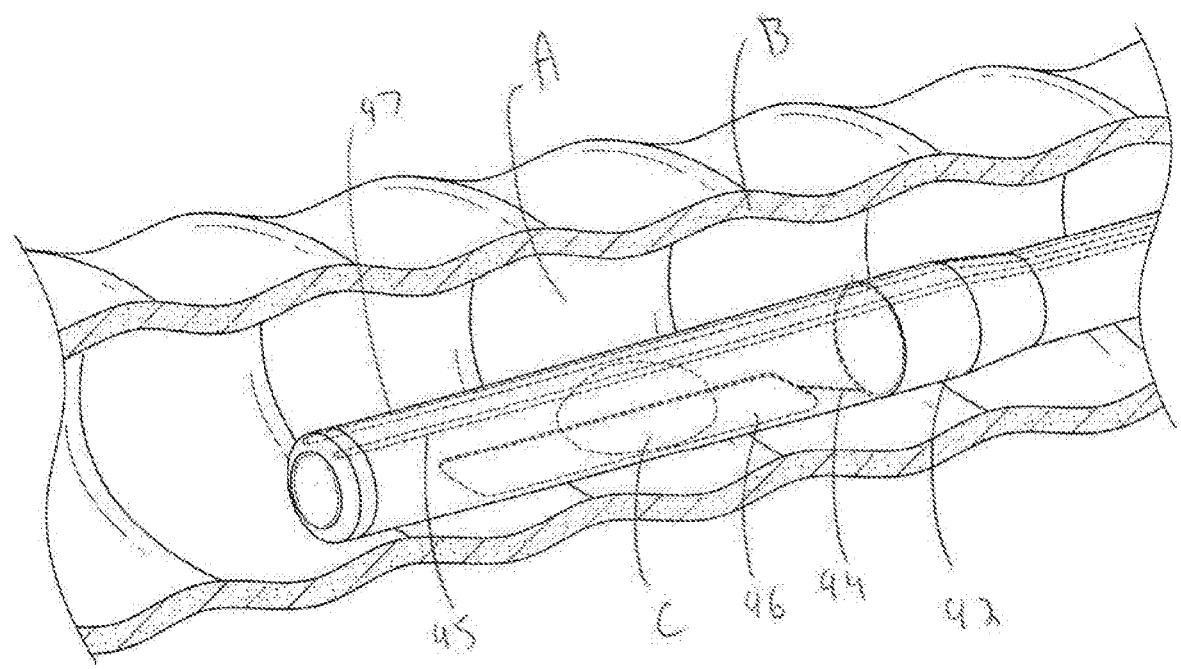
FIG. 20A is a perspective view of the distal portion of another alternate embodiment of the system showing the catheter in the collapsed (non-expanded) position.
Figure 20B:
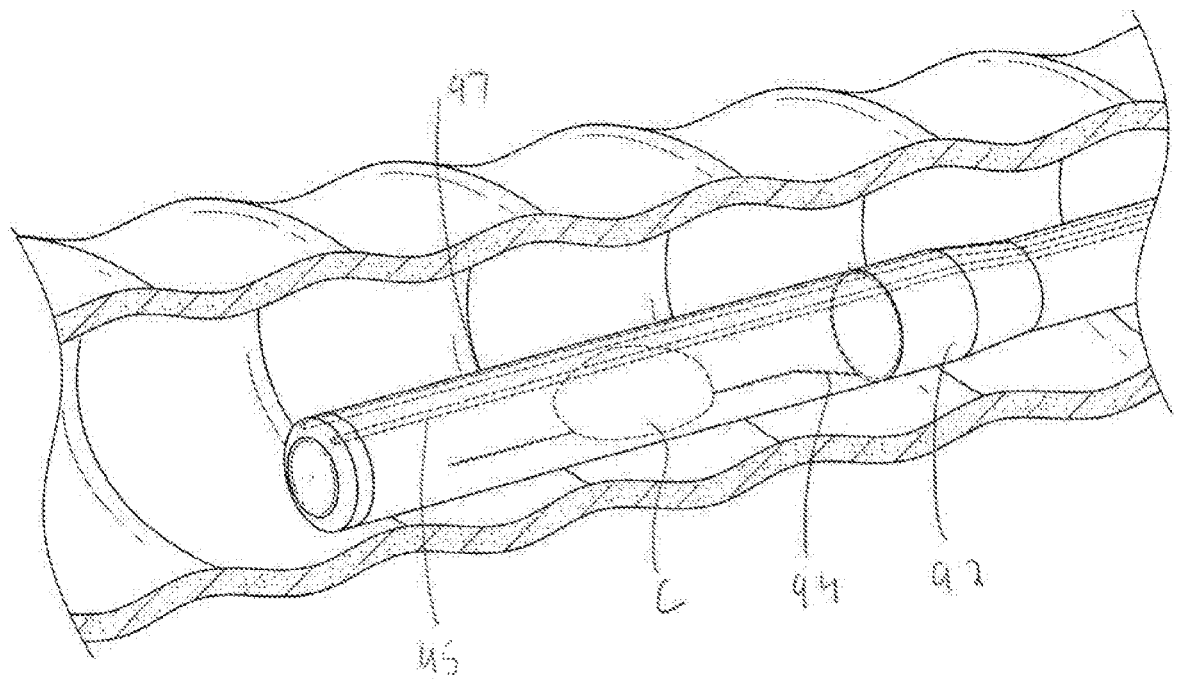
FIG. 20B is a view similar to FIG. 20A showing the window of the catheter closed.

As noted above, the window of the catheter can in certain embodiments be closable to capture tissue removed from the body, e.g., a polyp removed from the colon wall. FIGS. 20A and 20B illustrate such closable window in conjunction with catheter 92 which is identical to catheter 62 (except for the closable window) and expandable by pull wires 95, 97 (or alternatively push wires) which are identical to wires 64, 66. More specifically, a purse string suture 94 or other flexible elongated connector is attached to the window 96. When the polyp C (or other tissue) is positioned in the catheter 92 for removal after being dissected from the lumen wall, a proximal end of the suture 94, accessible to the user at a proximal portion of the catheter 92 outside the body, is pulled proximally, thereby applying a tension to the suture 94 to collapse the window 96 to transition the window 96 from the open position of FIG. 20A to the closed position of FIG. 20B. A locking mechanism can be provided to retain the suture 94 in the tensioned position to keep the window 96 closed. The suture can be attached to an edge of the window or alternatively extend around a portion of the entire perimeter. In some embodiments, the catheter material is sufficiently flexible so pulling the suture 94 collapses/closes the window 96. In some embodiments, a flexible material can be arranged around the perimeter of the window 96 which is folded or collapsed around the perimeter to keep the window open and is spreadable and closable by pulling of the suture to close the window. Other mechanisms and methods to close the window are also contemplated, such as a slidable member or shutter which can be pushed, pulled or slid laterally to close the window to capture the tissue within the catheter. Note such closable window can be utilized with any of the embodiments disclosed herein. The closed window helps to prevent or minimize seeding of the pathological tissue, e.g., cancerous tissue, during removal. That is, the target tissue, e.g., polyp, during its removal from the body is isolated from the surrounding innocent tissues.

Figure 21A:
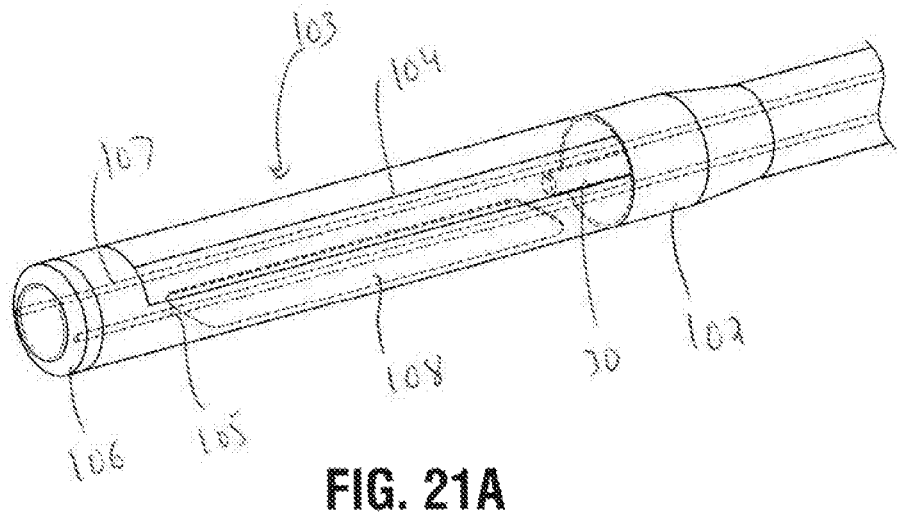
FIG. 21A is a perspective view of the distal portion of another alternate embodiment of the system showing the catheter in the collapsed insertion position.
Figure 21B:
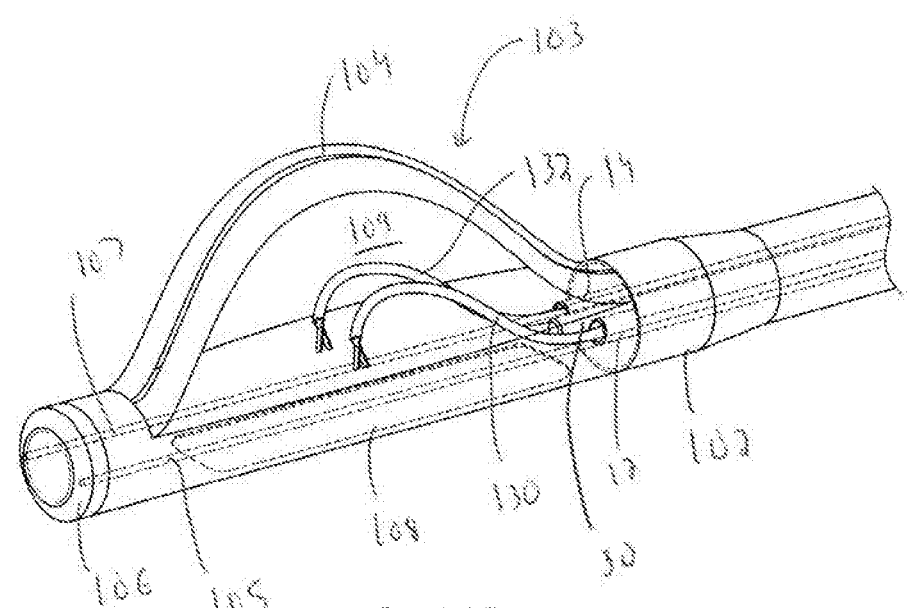
FIG. 21B is a view similar to FIG. 21A showing the catheter in the expanded position and two endoscopic instruments inserted into the expanded space.

FIGS. 21A and 21B illustrate an alternate embodiment of the catheter. The catheter 102 is identical to catheter 62 except that it is expandable due to a series of cutouts 104 formed in the catheter wall. When the distal region or distal cap 106 is pulled proximally by wires 105, 107, attached thereto at their distal ends, it flexes (buckles) the expandable region (portion) 103, formed by cutouts 104, to flex radially outwardly to the position of FIG. 21B, thereby moving the wall opposite the lesion in a direction away from the lesion as in the aforedescribed embodiments. This creates an asymmetrical working space 109 as in the previously described embodiments. In an alternate embodiment, a portion of the catheter proximal of the expandable portion can be pushed instead of pulled to flex (buckle) the expandable region of the catheter due to the flexibility created by the cutouts. Any of the aforedescribed embodiments of the tool channels and endoscopic instruments can be utilized with catheter 102 of FIGS. 21A and 21B. Tool channels 12, 14 and endoscopic instruments 130, 132 are shown by way of example, the instruments 130, 132 extending into the working space 109 created by the expandable member/portion 103 to increase the distance from the working tips of the endoscopic instruments 130, 132 to the window 108 and target tissue, e.g., polyp, as described above.

In alternative embodiments of the system of the present invention, the system can include floating (flexible) channels within the catheter. In one embodiment, the floating channels are fixed at their proximal and distal ends; in another embodiment the floating channels are fixed at their proximal ends but are unattached at their distal ends. The floating channels reduce the overall stiffness of the catheter (outer tube) which would otherwise be stiffer if the channels were fixed along their entire length and did not float within the catheter. The floating channels also reduce kinking of the tool channels (flexible guides) inserted through the floating channels and reduce kinking of the tools inserted through the tool channels (or inserted directly through the floating channels in the embodiments where the tool channels are not utilized). Floating channels which can be utilized are disclosed in application Ser. No. 14,622,831, filed Feb. 14, 2015, the entire contents of which are incorporated herein by reference.

The catheter in some embodiments can have a single lumen dimensioned to receive 1) an endoscope; and 2) two flexible channels in the form of flexible tubes that float inside the lumen. That is, the two floating channels have intermediate portions that can move radially (laterally) within the lumen of the catheter. Stated another way, the floating channels are unconstrained within the catheter so they can bend relative to the catheter so their bending action does not need to follow that of the catheter. In this manner, when the catheter is inserted in the body lumen and needs to bend to accommodate the curvatures of the body lumen, e.g., the gastrointestinal tract, the flexibility of the catheter is maintained since the floating channels can move within the lumen of the catheter, thereby increased flexibility is achieved. It should be understood that any of the systems disclosed herein could be provided with floating channels. Likewise, any of the systems disclosed herein could be provided without floating channels. The tool channels disclosed herein can be inserted through the floating channels or alternatively the endoscopic instruments can be inserted directly into the floating channels. Also, by providing a single lumen to receive the endoscope and the tool channels, rather than separate lumens which would require additional wall structure, a smaller diameter catheter can be provided which also reduces the overall stiffness of the catheter. The endoscope, e.g., endoscope 30, can in some embodiments also float within the lumen. That is, the endoscope can occupy only a certain region of the lumen and can move radially (laterally) within the lumen of catheter to increase the flexibility of the system. Thus, the endoscope can move relative to the catheter in a similar manner as the floating channels can move relative to the catheter.

The working instruments can include graspers for example. A dissecting/cutting instrument can be inserted through the flexible guide in the floating channel, or alternatively inserted through a working channel of the endoscope. Thus, various working instruments can be inserted through the flexible guides and endoscope channel(s).

The chamber.

The expandable members or portions (regions) disclosed herein form a retractor system that when expanded from its collapsed insertion position forms a working space expanding system and in certain surgical procedures a body lumen reshaping system which reshapes the body lumen to form an asymmetric space without stretching the body lumen wall beyond a point when it can be injured, e.g., lacerated by the stretching force, to increase the working space for the maneuverability of the endoscopic instruments. That is, the retractor system forms an expanded area within the body lumen for the surgeon to perform the surgical procedure. By reshaping the body lumen, the working space is maximized without overstretching the body lumen. Such working space maximization increases the distance between the target tissue and the end effectors (working tips) of the endoscopic instruments, hence improving maneuverability of the instruments during the surgical procedure. In such reconfiguring, the body lumen shape can be changed from a substantially circular cross-sectional configuration to a somewhat oval shape configuration where the walls are elongated. Thus, the expandable region changes the colon shape at the desired site to a narrower width, thereby reconfiguring the colon lumen, to increase working space for the instruments.

The expandable members of the embodiments disclosed herein can in some embodiments stabilize the luminal wall motion which may be more prominent in the gastrointestinal tract. This may facilitate the surgical procedure, particularly in the gastrointestinal tract.

Note that the various embodiments of the catheter described above are expandable to alter the working space within the body space or body lumen. As the working space is expanded, the distance between the instruments and the target tissue is increased, hence, facilitating the instruments' maneuverability and ability to perform more advanced surgical techniques inside the lumen, e.g., tissue retraction, dissection, repair. As the expandable region/portion expands, it may press on and deflect at least a portion of the luminal wall. As a result, the shape of the lumen can be changed depending on the size and shape of the expandable region, the extent of its expansion and the size and shape of the body lumen. In smaller diameter body lumens, such as the bowel, the expansion of the expandable region may substantially reshape the body lumen as described above. This reshaping can also occur in larger diameter body lumens. However, it should also be appreciated that in certain larger diameter body lumens, such as the stomach, and especially when insufflation is utilized for the surgical procedure, the body lumen may not necessarily be reshaped. However, even in this case, the expanded member (region) applies a radial force against the body wall to alter the working space. Therefore, whether the catheter is used in small or larger diameter working spaces/lumens, it advantageously moves the wall to increase the distance between the tips of the instruments and the target tissue, thereby functioning as a working space expanding system to facilitate access and maneuverability as described in detail above. As can also be appreciated, the dynamic nature of the expandable region with its controlled expansion enables the system to function as an organizer to adjust and optimize the distance between the tips of the instruments and the target tissue. Also note that in larger diameter body lumens, a symmetric chamber might also be able to be utilized, although not optimal.

Note the endoscopic instruments can be used for partial tissue resection, for example, submucosal or subserosal resection. The endoscopic instruments could also be utilized for full thickness tissue resection. The instruments enable removal of the lesion with healthy tissue margins, thereby providing a complete, en-block removal of the pathological lesion.

Without intending to be limited to any theory or mechanism of action, the above teachings were provided to illustrate a sampling of all possible embodiments rather than a listing of the only possible embodiments. As such, it should be appreciated that there are several variations contemplated within the skill in the art that will also fall into the scope of the claims.

The invention claimed is:

1. A system for endoscopic surgery within a body lumen of a patient comprising:
    a flexible catheter having a proximal portion, a distal portion, an expandable region comprising an expandable balloon disposed on a first side of the flexible catheter adjacent the distal portion,
    the flexible catheter having an access opening positioned on a second side of the catheter opposite the first side, and opposite the expandable balloon;
    the expandable region being expandable from a collapsed insertion configuration to an expanded configuration,
    the expandable region having an increased transverse dimension to provide an expanded chamber inside the expandable balloon,
    the access opening positioned to provide a window to access target tissue therethrough,
    the catheter including a lumen dimensioned to receive an endoscopic instrument therethrough such that a distal end of the endoscopic instrument is positionable within the expanded chamber and angled laterally within the expanded chamber to access the target tissue through the window,
    the lumen of the catheter having an opening at a distal end communicating with the chamber, the catheter further dimensioned to receive a visualization device to visualize the target tissue, and
    the endoscopic instrument received in the lumen of the catheter is movable independently of the visualization device.

2. The system of claim 1, wherein the catheter includes an elongated actuation member for expanding the expandable region and an actuator at the proximal portion of the catheter to move the elongated actuation member.

3. The system of claim 1, wherein the window is axially aligned with the expanded chamber.

4. The system of claim 1, wherein the expandable region includes a wall of the catheter expandable by an elongated member.

5. The system of claim 1, further comprising an articulation member for angling the distal portion of the catheter with respect to a longitudinal axis of the catheter.

6. The system of claim 1, wherein the expandable balloon has a U-shape forming a space within the U.

7. The system of claim 1, wherein the catheter has a seal at a distal end and the visualization device is movable through the seal to visualize distally of the catheter.

8. The system of claim 1, wherein the expandable region has a wall thickness that is thinner than other regions of the flexible catheter to facilitate expansion.

9. The system of claim 1, wherein the expandable region is configured to the expanded configuration via movement of a wire coupled to the flexible catheter.

10. A flexible catheter for endoscopic surgery within a body lumen of a patient comprising:
    a proximal portion and a distal portion, the distal portion having an expandable region expandable from a collapsed insertion configuration to an expanded configuration, the expandable region comprising an expandable balloon,
    the expandable region disposed on a first side of the flexible catheter, the expandable region having an increased transverse dimension to form an expanded chamber inside the expandable balloon,
    the catheter having an access opening on a second side of the catheter opposite the first side, and opposite the expandable balloon, to provide access to target tissue therethrough, and
    the catheter including a lumen having a distal opening communicating with the expanded chamber;
    wherein the chamber inside the expandable balloon is configured to receive a working instrument therein such that a distal end of the working instrument is positionable within the expanded chamber and angleable laterally within the expanded chamber to access the target tissue through the window.

11. The catheter of claim 10, wherein the balloon has a U-shaped cross-sectional configuration.

12. The catheter of claim 10, wherein the catheter includes a seal at its distalmost end.

13. The catheter of claim 10, further comprising an elongated member axially movable to move the expandable region to the expanded configuration.

14. The catheter of claim 10, wherein the expandable region is expandable due to a series of cutouts formed in the catheter wall.

15. A method of minimally invasively treating tissue comprising:
    a) inserting into a body lumen of a patient an endoscopic device having a window and an expandable portion comprising an expandable balloon in a collapsed configuration, the expandable portion having an inner wall, the expandable portion comprising an expandable balloon formed on a first side of the endoscopic device, the window formed in a second side of the expandable balloon opposite the first side and opposite the expandable balloon;
    b) after insertion of the endoscopic device into the body lumen, expanding the expandable portion from the collapsed configuration to an expanded configuration to create a chamber inside the expandable balloon, the chamber having an increased transverse dimension to increase a distance inside the expandable balloon between the inner wall of the expandable portion and the window;
    c) inserting a distal portion of a working instrument into the chamber inside the expandable balloon, the working instrument extending through a first channel in the endoscopic device, and the distal portion of the working instrument extending laterally within the chamber with respect to a longitudinal axis of the endoscopic device;
    d) visualizing the distal portion of the working instrument by a visualization device; and
    e) inserting a tip of the working instrument through the window to access target tissue.

16. The method of claim 15, wherein the step of expanding the expandable portion expands the chamber to only one side of the longitudinal axis of the endoscopic device and retracts tissue opposite the target tissue.

17. The method of claim 15, wherein the step of expanding the expandable portion includes a step of expanding the balloon.

18. The method of claim 15, wherein the step of expanding the expandable portion includes a step of axially moving an elongated member positioned in the endoscopic device.

19. The method of claim 18, wherein moving the elongated member expands a series of cutouts formed in the catheter wall.

* * * * *